United States Patent
Srinivasan

(10) Patent No.: US 10,682,393 B2
(45) Date of Patent: *Jun. 16, 2020

(54) GLIAL CELL LINE DERIVED NEUROTROPHIC FACTOR, OBESITY, AND OBESITY-RELATED DISEASES AND CONDITIONS

(71) Applicants: Emory University, Atlanta, GA (US); U.S. Government represented by the United States Department of Veterans Affairs, Washington, DC (US)

(72) Inventor: Shanthi Srinivasan, Atlanta, GA (US)

(73) Assignees: Emory University, Atlanta, GA (US); The United States Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/037,268

(22) Filed: Jul. 17, 2018

(65) Prior Publication Data

US 2018/0326009 A1 Nov. 15, 2018

Related U.S. Application Data

(63) Continuation of application No. 15/003,324, filed on Jan. 21, 2016, now Pat. No. 10,052,362, which is a continuation-in-part of application No. 14/007,374, filed as application No. PCT/US2012/036495 on May 4, 2012, now abandoned.

(60) Provisional application No. 61/503,120, filed on Jun. 30, 2011, provisional application No. 61/482,880, filed on May 5, 2011.

(51) Int. Cl.
*A61K 38/18* (2006.01)
*C07K 14/475* (2006.01)

(52) U.S. Cl.
CPC .......... *A61K 38/185* (2013.01); *C07K 14/475* (2013.01)

(58) Field of Classification Search
CPC ............................ A61K 38/185; C07K 14/475
See application file for complete search history.

(56) References Cited

U.S. PATENT DOCUMENTS

| 10,052,362 B2 | 8/2018 | Srinivasan |
| 2004/0242472 A1 | 12/2004 | Shelton |
| 2008/0187522 A1 | 8/2008 | Srinivasan |

FOREIGN PATENT DOCUMENTS

RU 2197240 1/2003

OTHER PUBLICATIONS

Hoane et al., Experinnenatal Neurology 160(1999): 235-243.*
Creedon et al. Neurturin shares receptors and signal transduction pathways with glial cell line-derived neurotrophic factor in sympathetic neurons, Proc. Natl. Acad. Sci. USA, vol. 94, pp. 7018-7023,1997.
Hoane et al. Differential in Vivo Effects of Neurturin and Glial Cell-Line-Derived Neurotrophic Factor, Experimental Neurology 160, 235-243 (1999).
Marks et al. Protein structure prediction from sequence variation, Nat Biotechnol. 2012, 30(11):1072-80.
Mwangi et al., Glial cell line-derived neurotrophic factor enhances human islet posttransplantation survival, Transplantation. 2011, 92(7):745-51.
Mwangi et al., Glial cell line-derived neurotrophic factor protects against high-fat diet-induced obesity. Am J Physiol Gastrointest Liver Physiol 306: G515-G525, 2014.
Mwangi et al. Glial cell line-derived neurotrophic factor protects against high-fat diet-induced hepatic steatosis by suppressing hepatic PPAR-γ expression. Am J Physiol Gastrointest Liver Physiol. 2016, 310(2):G103-16.
Mwangi et al. Glial Cell Line-Derived Neurotrophic Factor Enhances Autophagic Flux in Mouse and Rat Hepatocytes and Protects Against Palmitate Lipotoxicity, Hepatology. 2019, 69(6):2455-2470.
Ng et al. Predicting the Effects of Amino Acid Substitutions on Protein Function, Annu. Rev. Genomics Hum. Genet. 2006, 7:61-80.
Parkash et al. The Structure of the Glial Cell Line-derived Neurotrophic Factor-Coreceptor Complex, The Journal of Biological Chemistry vol. 283, No. 50, pp. 35164-35172.
Parkash et al. Comparison of GFL-GFRa complexes: further evidence relating GFL bend angle to RET signalling, Acta Crystallogr Sect F Struct Biol Cryst Commun. 2009, 65(Pt 6):551-8.
Shi et al. Glial Cell Line-Derived Neurotrophic Factor Gene Transfer Exerts Protective Effect on Axons in Sciatic Nerve Following Constriction-Induced Peripheral Nerve Injury, Human Gene Therapy 22:721-731 (2011).
UniProtKB: locus GDNF_HUMAN, accession P39905, sequence updated: Feb. 1, 1995.
Vakili et al. Glial Cell Line-Derived Neurotrophic Factor-Induced Mice Liver Defatting:A Novel Strategy to Enable Transplantation of Steatotic Livers, Liver Transplantation 22, 459-467, 2016, AASLD.

* cited by examiner

*Primary Examiner* — Robert C Hayes
(74) *Attorney, Agent, or Firm* — Emory Patent Group

(57) ABSTRACT

The disclosure relates to therapeutic methods for regulating weight gain, metabolic syndrome, and insulin resistance. In certain embodiments, the disclosure relates to methods of treating or preventing obesity, metabolic syndrome, or insulin resistance by administering an effective amount of a pharmaceutical composition comprising one or more GDNF receptor agonists to a subject in need thereof.

8 Claims, 22 Drawing Sheets

Specification includes a Sequence Listing.

GLIAL CELL LINE DERIVED NEUROTROPHIC FACTOR, OBESITY, AND OBESITY-RELATED DISEASES AND CONDITIONS

CROSS-REFERENCE TO RELATED APPLICATIONS

This application is a continuation of U.S. patent application Ser. No. 15/003,324 filed Jan. 21, 2016, which is a continuation-in-part of U.S. patent application Ser. No. 14/007,374 filed Sep. 25, 2013, which is the National Stage of International Application No. PCT/US2012/036495 filed May 4, 2012, which claims the benefit of U.S. Provisional Application No. 61/503,120 filed Jun. 30, 2011 and U.S. Provisional Application No. 61/482,880 filed May 5, 2011. The entirety of each of these applications is hereby incorporated by reference for all purposes.

STATEMENT REGARDING FEDERALLY SPONSORED RESEARCH OR DEVELOPMENT

This invention was made with government support under E01 DK080684 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 11119USCON_ST25.txt. The text file is 17 KB, was created on Jul. 17, 2018, and is being submitted electronically via EFS-Web.

FIELD

The disclosure relates to therapeutic methods for regulating weight gain, metabolic syndrome, and insulin resistance. In certain embodiments, the disclosure relates to methods of treating or preventing obesity, metabolic syndrome, or insulin resistance by administering an effective amount of a pharmaceutical composition comprising one or more GDNF receptor agonists to a subject in need thereof.

BACKGROUND

Obesity is an increasing problem in the United States, with a prevalence of approximately 25% of the population. Increased visceral fat causes dysfunction of various organs and abnormal production of adipokines. Excessive body weight is a risk factor for an array of complications, including cardiovascular disease, several forms of cancer, type 2 diabetes, infertility, sexual dysfunction, and osteoarthritis. Obesity is also increasingly common in children; the rate of childhood obesity in the United States has tripled during the past 30 years. The increasing prevalence of obesity correlates with a significant increase in the prevalence of type 2 diabetes in children. Efforts to treat obesity and its related diseases and conditions, including metabolic syndrome and insulin resistance, have taken varying approaches ranging from bariatric surgery to pharmaceuticals. See, e.g., U.S. Pat. No. 5,234,454 (gastric balloon), U.S. Pat. No. 7,945,323 (stimulating the pituitary gland via an implant), and U.S. Pat. No. 6,969,702 (Exendin-4, a GLP-1 receptor agonist). However, there remains a need to identify improved methods for regulating weight gain.

Obesity is characterized by the presence of increased visceral and subcutaneous fat. The accumulation of intra-abdominal visceral fat strongly correlates with metabolic dysfunction and cardiovascular disease. The complex pathophysiology leading to excessive adipose tissue accumulation includes excessive caloric intake, reduced energy expenditure and enhanced adipogenesis. Despite the prevalence of obesity and its associated risks, few therapeutic options are available. Orlistat and Phentermine are two available pharmaceutical options available, but their efficacy is hindered long-term due to potential complications. The desire to treat and prevent obesity as well as its complications has led to considerable interest in obesity-related research.

The mass of adipose tissue is determined by a balance between energy intake and expenditure. Enhanced energy expenditure in cells can result in weight loss due to a net negative balance of caloric intake vs. caloric expenditure. Total energy expenditure includes physical activity, basal metabolism, and adaptive thermogenesis. Increased energy expenditure in adipocytes is associated with enhanced mitochondrial biogenesis and oxygen consumption. The PI3K pathway has been implicated in the regulation of energy homeostasis and can result in enhanced expression of PGC-1α. PGC-1α regulates energy homeostasis in response to environmental and nutritional stimuli. PGC-1α expression is reduced in obesity. Further, neuronal denervation has been associated with a reduction in PGC-1α expression. PGC-1α regulates multiple transcription factors to stimulate mitochondrial metabolic capacity. Mitochondrial content and oxygen consumption are reduced in the adipose tissue in high-fat diet induced obesity models. Adipocytes respond to adrenergic stimulation with catabolic reactions including lipolysis and non-shivering thermogenesis, the latter by virtue of the mitochondrial uncoupling protein-1 (UCP1) which is specifically expressed in brown adipose tissue (BAT) and regulated by β-adrenergic receptors, in particular the β3-adrenergic receptor. Anabolic functions such as lipogenesis are suppressed by adrenergic stimulation. As indicated by its name, UCP-1 uncouples oxidative phosphorylation from ATP synthesis and, instead, releases the energy stored in the proton gradient across the mitochondrial membrane as heat.

Insulin resistance occurs when peripheral tissues require an elevated amount of insulin and is associated with obesity. Although the pancreatic β cell mass is capable of increasing as insulin demand increases, its plasticity is limited. When the β cells can no longer produce sufficient insulin to meet the demand, hyperglycemia occurs and type 2 diabetes develop. Adipocytes, which are increased in the obese, are believed to play a role in this process. Adipocytes do not simply store energy; they also produce adiponectin, leptin, and various cytokines. They are believed to exert significant physiological effects, such as reducing glucose uptake in the periphery by the release of free fatty acids. Furthermore, obesity-related adipocyte apoptosis leads to inflammation, resulting in a cascade of deleterious physiological events, possibly including the inhibition of insulin signaling. Unfortunately, current anti-diabetic drugs such as thiazolidinediones are associated with further weight gain in part due to stimulation of peroxisome proliferator-activated receptor-γ (PPAR-γ) induced adipogenesis.

Glial cell line derived neurotrophic factor (GDNF) is a GDNF family receptor alpha-1 (GFRα-1) agonist, important for the differentiation and survival of neurons. GDNF signals through its receptors, including Ret and GFR-1α, by activation of the PI3K and MAPK pathways. GDNF has been contemplated as a neuromodulatory therapeutic agent for Parkinson's Disease. See, e.g., U.S. Published Patent Application No. 2008/0187522. Fu, et al. disclose intravenous treatment of experimental Parkinson's disease in the mouse with an IgG-GDNF fusion protein that penetrates the blood-brain barrier. Brain Res. 2010 Sep. 17; 1352:208-13.

The effect of neurotrophic factors on weight regulation is not entirely understood. See e.g., Bence, et al. Neuronal PTP1B regulates body weight, adiposity and leptin action. Nat Med. 2006. 12:917-924. Turner, et al. disclose hypothalamic rAAV-mediated GDNF gene delivery ameliorates age-related obesity. Neurobiol Aging. 2006 March; 27(3): 459-70. The effect of GDNF weight loss was thought to be mediated via its effects on dopaminergic neurons in the hypothalamus.

SUMMARY

This disclosure provides that GDNF can be used to treat weight gain and related diseases and conditions. The disclosure pertains to methods of use and compositions of GDNF and other GFR agonists for weight control and related diseases and conditions.

In certain embodiments, the disclosure relates to methods of regulating weight gain by orally, systematically, or peripherally administering an effective amount of one or more GDNF receptor agonists to a subject in need thereof. In certain embodiments, the subject is in need thereof because the subject is obese, overweight, has an excessive body fat ratio (e.g., fat is in excess of 20%, 25%, or 30% of total body weight) or normal weight. In certain embodiments, the method of treatment is used to prevent weight gain. In certain embodiments, the method of treatment is used to induce weight loss. In certain embodiments, the method of treatment is used to decrease food intake. In certain embodiments, the method of treatment is used to inhibit weight gain despite the subject consuming a high fat diet. In certain embodiments, the method of treatment is used to reduce body fat. In certain embodiments, the method of treatment is used to decrease the expression of genes associated with lipogenesis and/or adipogenesis including, but not limited to, CD36, FASN, PPAR-γ (a key transcriptional activator of adipocyte differentiation), fatty acid binding protein 4, and SREBF1. In certain embodiments, the method of treatment is used to increase the expression of genes associated with beta oxidation including, but not limited to, peroxisome proliferator-activated receptor-γ coactivator-1α (PGC1α), UCP2, and UCP3. In certain embodiments, the method of treatment is used to increase the expression of genes associated with beta oxidation including, but not limited to, UCP1, CAC and Kat. In certain embodiments, the method of treatment is used to reduce expression of beta oxidation genes in white adipose tissue. In certain embodiments, the method is used to increase energy utilization.

In certain embodiments, the method is used to increase basal metabolism. In certain embodiments, the method of treatment is combined with one or more other weight loss therapeutics as described herein. In certain embodiments, the method of treatment is recombinant GDNF, a GDNF homolog, ortholog, peptide, mutant, small molecule mimetic, and/or derivative. In certain embodiments, the method of treatment is administered in one or more routes including, but not limited to, over-expression of one or more GDNF receptor agonists in transgenic animals, subcutaneous injection, intraperitoneal injection, intradermal injection, intramuscular injection, intravenous administration, oral administration either in pill form or in solution, topical administration, transdermal administration, gene therapy in which a viral vector is used to induce or increase expression of one or more GDNF receptor agonists, intranasal administration, ocular administration, rectal administration, cellular therapy using GDNF-expressing cells, or any combination thereof. In some embodiments, the viral vector is targeted to peripheral tissue.

In certain embodiments, the disclosure relates to method of treating metabolic syndrome by administering one or more GDNF receptor agonists to a subject in need thereof. In certain embodiments, the subject is in need thereof because the subject is diagnosed with, suspected of, susceptible to, or exhibiting symptoms of metabolic syndrome. In certain embodiments, the method of treatment is combined with one or more other metabolic syndrome therapeutics as described herein. In certain embodiments, the method of treatment is recombinant GDNF, a GDNF homolog, analog, peptide, mutant, small molecule mimetic, or derivative. In certain embodiments, the method of treatment is administered in one or more routes including, but not limited to, over-expression of one or more GDNF receptor agonists in transgenic animals, subcutaneous injection, intraperitoneal injection, intradermal injection, intramuscular injection, intravenous administration, oral administration either in pill form or in solution, topical administration, transdermal administration, gene therapy in which a viral vector is used to induce or increase expression of one or more GDNF receptor agonists, intranasal administration, ocular administration, rectal administration, cellular therapy using GDNF-expressing cells, or any combination thereof. In some embodiments, the treatment is administered orally or systemically. In some embodiments, the treatment is administered peripherally.

In certain embodiments, the disclosure relates to method of treating insulin resistance by administering one or more GDNF receptor agonists to a subject in need thereof. In certain embodiments, the subject is in need thereof because the subject is diagnosed with, suspected of, susceptible to, or exhibiting symptoms of insulin resistance. In certain embodiments, the method of treatment is combined with one or more other insulin resistance therapeutics as described herein. In certain embodiments, the method of treatment is recombinant GDNF, a GDNF homolog, analog, peptide, mutant, small molecule mimetic, or derivative. In certain embodiments, the method of treatment is administered in one or more routes including, but not limited to, over-expression of one or more GDNF receptor agonists in transgenic animals, subcutaneous injection, intraperitoneal injection, intradermal injection, intramuscular injection, intravenous administration, oral administration either in pill form or in solution, topical administration, transdermal administration, gene therapy in which a viral vector is used to induce or increase expression of one or more GDNF receptor agonists, intranasal administration, ocular administration, rectal administration, cellular therapy using GDNF-expressing cells, or any combination thereof. In some embodiments, the treatment is administered systemically. In some embodiments, the treatment is administered peripherally. In certain embodiments, the method of treatment is used to maintain normal fasting blood glucose level.

In certain embodiments, the subject is a mammal, typically a human.

In certain embodiments, the disclosure relates to a method of treating hepatic steatosis by administering one or more GDNF receptor agonists to a subject in need thereof. In certain embodiments, the disclosure relates to treating or preventing conditions or diseases disclosed herein, such as, asthma, Blount's disease, cardiovascular disease, gallstones, hypertension, intracranial hypertension, insulin resistance, metabolic syndrome, obesity, osteoarthritis, Pickwickian syndrome, polysystic ovary syndrome, sleep apnea, steatohepatitis, type 2 diabetes, and/or any other diseases and conditions associated with obesity and/or type 2 diabetes, by administering an effective amount of a GDNF receptor agonist, such as a polypeptide comprising GDNF sequence, conserved variant, or active fragment.

In some embodiments, the subject is diagnosed with asthma, Blount's disease, cardiovascular disease, gallstones, hypertension, intracranial hypertension, insulin resistance, metabolic syndrome, obesity, osteoarthritis, Pickwickian syndrome, polycystic ovary syndrome, sleep apnea, steatohepatitis, type 2 diabetes, and/or any other diseases and conditions associated with obesity and/or type 2 diabetes.

In certain embodiments, the GDNF receptor agonist is a polypeptide comprising or consisting essentially of the amino acid sequence described in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 or SEQ ID NO:10 including sequences that have 70%, 80%, 90%, or 95% sequence identity to these sequences or conserved variants or derivatives thereof. In certain embodiments, the GDNF receptor agonist is capable of inducing increased expression of PGC-1α. Peroxisome proliferator-activated receptor gamma coactivator 1-alpha (PGC-1alpha) is a protein that in humans is encoded by the PPARGC1A gene. In certain embodiments, the GDNF receptor agonist may be human GDNF or human pre-pro GDNF. In certain embodiments, the GDNF receptor agonist may be mature human GDNF. In certain embodiments, the GDNF receptor agonist may be an ortholog of human GDNF or human pre-pro GDNF.

In certain embodiments, the disclosure relates to the use of a GDNF receptor agonist, typically recombinant GDNF protein, in the production of a weight control medicament for the treatment of weight control, insulin resistance, and/or metabolic syndrome.

In certain embodiments, the subject is a human male weighing over 180 pounds or the subject is a human female weighing over 160 pounds.

In certain embodiments, the disclosure relates to pharmaceutical compositions comprising a GDNF receptor agonist and a pharmaceutically acceptable excipient. In certain embodiments, the GDNF receptor agonist is recombinant GDNF protein, a GDNF homolog, ortholog, mutant, small molecule mimetic, or derivative. In certain embodiments, the GDNF receptor agonist comprises a polypeptide comprising the amino acid sequence described in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 or SEQ ID NO:10 including sequences that have 70%, 80%, 90%, or 95% sequence identity to these sequences or conserved variants or active fragments thereof. In certain embodiments, the pharmaceutical composition is in the form of a pill, capsule, tablet, or aqueous saline buffer solution optionally comprising one or more saccharides. In certain embodiments, the pharmaceutical composition comprises a second active ingredient.

In certain embodiments, the disclosure contemplates the production of a medicament for uses disclosed herein.

DETAILED DESCRIPTION

Figure 1A:
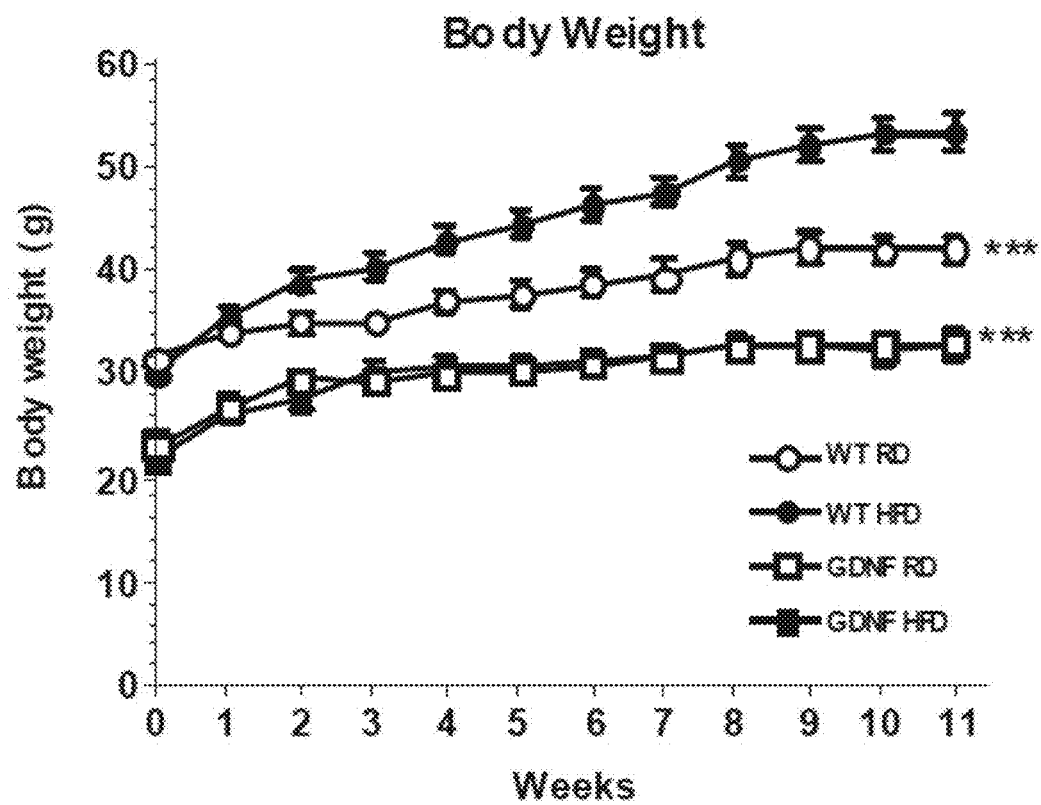
FIG. 1A shows data indicating GDNF-tg mice are protected against high fat diet-induced obesity, hyperleptinemia, hyperlipidemia and hypertriglyceridemia. Body weight and weight gain.
Figure 1A:
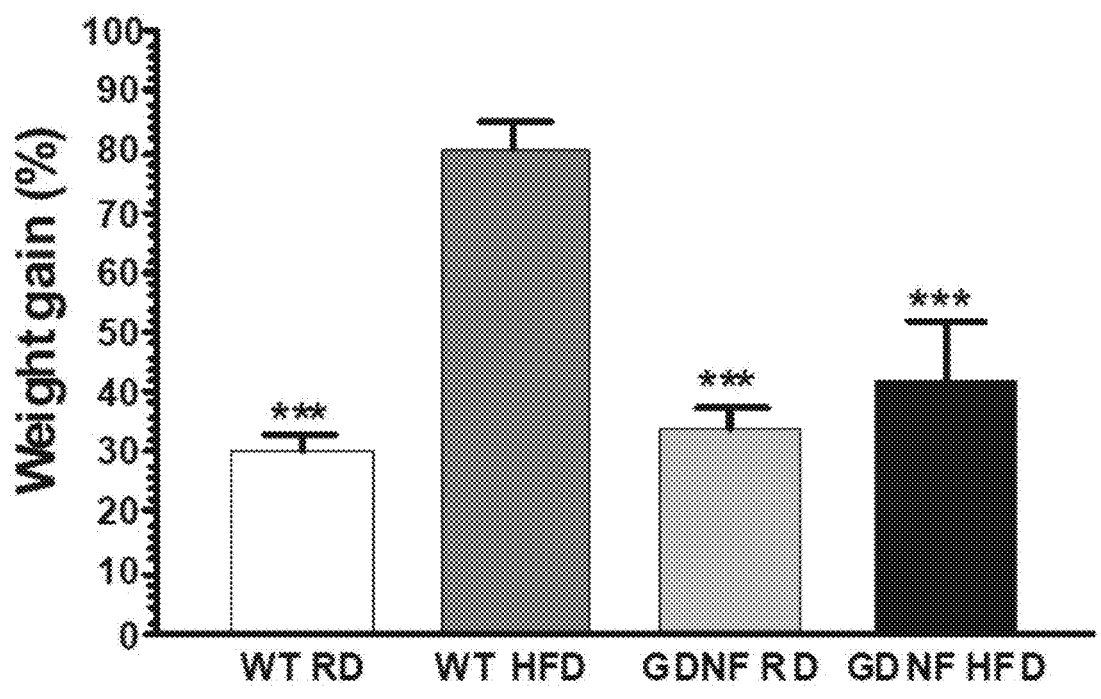

It has been discovered, as disclosed herein, that the over-expression of GDNF in glia results in resistance to high fat diet induced weight gain compared with normal GDNF expression. Furthermore, both visceral fat (epididymal fat pad) and renal fat were reduced. The over-expression of GDNF also mitigated blood glucose despite the consumption of a high fat diet, which is consistent with GDNF-induced amelioration of the metabolic syndrome phenotype. There was also significantly improved glucose tolerance, reduced levels of serum leptin, and increased adiponectin, indicating improved insulin sensitivity. Improved insulin sensitivity was also observed by an improved blood glucose response to the injection of insulin. Finally, GDNF over-expression reduced hepatic steatosis (hepatic fat) despite a high fat diet. These differences were observed despite no significant difference in food consumption.

Despite no difference in ambulatory movement, GDNF over-expression resulted in significantly higher basal metabolic rates (reflected by $CO_2$ production and oxygen consumption) indicating increased energy expenditure. The lean body mass assessed by NMR (Nuclear Magnetic resonance Imaging) was also significantly lower with GDNF over-expression.

It is known that GDNF signals through the receptors Ret and GFR-1α. A peripheral or systemic method of delivering GDNF may be facilitated if a target could be found outside of the brain. Consequently, as disclosed herein, expression of Ret and GFR-1α was discovered in WAT (white adipose tissue) of mice (both with and without GDNF over-expression) using RT-PCR. GDNF and its receptors C-Ret and GFR-1α are also present on human adipocytes. This presents a potential target for GDNF-based therapies.

Given the presence of GDNF receptors in adipose tissue, the next step is whether GDNF can alter genes regulating energy expenditure in that adipose tissue. PGC-1α is a transcriptional coactivator that is involved in the up-regulation of mitochondrial biogenesis and fatty acid oxidation. Uncoupling proteins (UCP) are a family of proteins involved in the regulation of lipid oxidation as well as the regulation of energy expenditure. Increased PGC-1α may induce mitochondrial biogenesis. Using Real-time PCR, as disclosed herein, PGC-1α and UCP3 gene expression was upregulated in the WAT of HF-diet fed mice over-expressing GDNF, indicating a mechanism for increased energy expenditure. GDNF over-expression also reduced the expression of genes related to adipocyte differentiation including PPAR-γ, FASN, and FABP4 in WAT. Down-regulation of these three genes was also achieved using 3T3L-1 cells in vitro.

Injection of GDNF resulted in measurable, significantly elevated levels of serum GDNF in vivo. It has been discovered, as disclosed herein, that the administration of GDNF induces phosphorylation of Akt and MAPK in vitro. The GDNF-mediated inhibition of adipogenesis was reversed in the presence of the MAPK inhibitor, PD98059. This effect was mirrored by the administration of GDNF in vivo via injection, resulting in a significant increase in pAKt in WAT.

It is believed that the systemic or peripheral administration of GDNF will enhance energy metabolism in adipocytes by activating Akt and switching on catabolic pathways, enhancing oxidative metabolism, and/or enhancing mitochondrial biogenesis.

Systemic or peripheral delivery of GDNF will result in reduced weight gain, an improved lipid profile, improved glucose tolerance, lower percentage of body, increased energy expenditure, and/or increased lipolysis versus control therapy.

Experimental data demonstrates that (i) GDNF inhibits high fat diet induced weight gain and resultant metabolic syndrome, (ii) receptors for GDNF are expressed in human and murine adipose tissue (iii) GDNF-tg mice have higher basal metabolic rates as assessed by indirect calorimetry, (iv) WAT from GDNF-tg mice have increased expression of genes regulating energy expenditure. In vitro data in 3T3-L1 cells show that GDNF inhibits the process of adipogenesis through its receptor Ret. Together these data demonstrate an important role for GDNF in regulating high-fat diet induced weight gain. Glial cell line derived neurotrophic factor (GDNF) improves energy expenditure with a combined reduction in adipogenesis; outcomes that have not been previously achievable with current FDA approved drugs for obesity.

Adipocytes are highly specialized cells that play a crucial role in energy balance of most vertebrates by providing the ability to synthesize and deposit fat during times of positive energy balance in preparation for periods of food deprivation 18. In modern society, however, excess adipose tissue leading to obesity with its associated diseases such as diabetes is a major health problem. The biological events leading to obesity are characterized by changes in cell properties of adipocytes and may include an increase in the number or size or both. With excess energy intake, there is an increase in lipogenesis and storage of triacylglycerol (TAG) as lipid droplets in adipose tissue that causes enlarged adipocytes (hypertrophy). Further, adipocytes can also increase in number (proliferation). In addition, precursor cells, preadipocytes, are recruited to become adipocytes (differentiation). Our studies demonstrate a role for GDNF in modulating adipogenesis in the pathophysiology of obesity.

Experiments herein indicate an important role GDNF in balancing energy homeostasis. Adipose tissue plays an active role in energy balance. GDNF induces increased thermogenesis. Although it is not intended that embodiments of the disclosure be limited by any particular mechanism, it is believed that GDNF regulates weight gain through modulation of energy expenditure. Total energy expenditure includes physical activity, basal metabolism and adaptive thermogenesis. Increased energy expenditure in adipocytes is associated with enhanced mitochondrial biogenesis and oxygen consumption. The enhanced expression of Peroxisome proliferator-activated receptor-γ coactivator-1a (PGC-1α) has been implicated in the regulation of energy homeostasis. PGC-1α regulates energy homeostasis in response to environmental and nutritional stimuli. PGC-1α expression is reduced in obesity. Further, neuronal denervation has been associated with a reduction in PGC-1α expression. PGC-1α regulates multiple transcription factors to stimulate mitochondrial metabolic capacity. Mitochondrial content and oxygen consumption are reduced in the adipose tissue in high-fat diet induced obesity models. Adipocytes respond to adrenergic stimulation with catabolic reactions including lipolysis and non-shivering thermogenesis, the latter by virtue of the mitochondrial uncoupling protein-1 (UCP1) which is specifically expressed in brown adipose tissue (BAT) and regulated by β-adrenergic receptors, in particular the β3-adrenergic receptor. Anabolic functions such as lipogenesis are suppressed by adrenergic stimulation. As indicated by its name, UCP-1 uncouples oxidative phosphorylation from ATP synthesis and, instead, releases the energy stored in the proton gradient across the mitochondrial membrane as heat.

Experiments herein indicate that GDNF-tg mice have increased expression of UCP-2 and UCP-3. The second major mechanism involved in GDNF-regulation of obesity is through modulating adipogenesis. Adipocytes are derived from mesenchymal stem cells, which have the potential to differentiate into myoblasts, chondroblasts, osteoblasts or adipocytes. The adipocyte formation includes alteration of cell shape and a complex sequence of gene changes leading to storage of lipid. PPAR-γ (a member of the nuclear hormone receptor family) and CCAAT/enhancer binding protein-alpha (C/EBP-α) are transcription factors influencing adipocyte differentiation. Another transcription factor induced very early during adipocyte differentiation is sterol regulatory element binding protein-1c (SREBP-1c). During the terminal phase of differentiation there is an increase in the enzymes involved in fatty acid metabolism such as acetyl coA carboxylase (ACC), fatty acid synthase (FASN), lipoprotein lipase (LPL) and hormone-sensitive lipase (HSL). In addition there is an increase in adipose tissue-specific products such adipocyte-specific fatty acid binding protein (aP2 or FABP4), fatty acid translocase (CD36) and perilipin (a lipid droplet-associated protein). The signal transduction pathways involved in the regulation of adipogenesis include the MAPK pathway and AMP-activated protein kinase (AMPK). Experiments herein indicate GDNF-induced suppression of adipogenesis and lipogenesis as seen by a reduction in genes regulating both processes in the WAT of GDNF-tg mice. In the GDNF-tg mice there was increase fat utilization and reduced fat synthesis. Genes associated with fatty acid uptake including LpL, Fabp, CD36 were increased in GDNF-tg mice, as well as genes associated with β-oxidation resulting in utilization of fatty acids. GDNF blocked the expression of mRNA involved in adipogenesis.

Another potential mechanism of GDNF regulation of body fat is through lipolysis. Our experiments in vitro showed no difference in lipolytic pathways in vehicle vs. GDNF treated adipoctyes in culture.

WT and GDNF-tg mice did not have different food consumption measurements and the data seemed to be independent of food as indicated by pair feeding experiments. Experiments herein demonstrate a role for GDNF and its downstream targets in the regulation of obesity.

GDNF

As used herein, the term "GDNF" refers to glial cell derived neurotrophic factor. Human GDNF has amino acid sequence provided in GenBank: CAG46721.1. GDNF plays an important role in neuronal differentiation and survival. The GDNF receptors include GFRal, GFRα2, GFRα3, and GFRα4, with GFRal being the typical receptor. cRET is also involved with GDNF binding and may also serve to increase binding affinity between GDNF and GFR. Both GFR and cRET are expressed in white adipose tissue in both humans and mice.

Human GDNF variant 1 is set forth in SEQ ID NO: 1, MKLWDVVAVCLVLLHTASAFPLPAGKRPPEAPAE-DRSLGRRRAPFALSSDSNMPED YPDQFDDVMD-FIQATIKRLKRSPDKQMAVLPRRERNRQAAAANPEN-SRGKGRRGQR GKNRGCVLTAIHLNVTDLGLGYETKEELIFRYC-SGSCDAAETTYDKILKNLSRNRRLV SDKVGQACCR-PIAFDDDLSFLDDNLVYHILRKHSAKRCGCI.

Human GDNF variant 2 is set forth in SEQ ID NO: 2, MKLWDVVAVCLVLLHTASAFPLPAANMPEDYP-DQFDDVMDFIQATIKRLKRSPDKQ MAVLPRRERN-RQAAAANPENSRGKGRRGQRGKNRGCVLTAIHLN-VTDLGLGYETK EELIFRYCSGSCDAAETTYDKILKNLSRNRRLVSDK-VGQACCRPIAFDDDLSFLDDNL VYHILRKH-SAKRCGCI.

Human GDNF variant 3 is set forth in SEQ ID NO: 3, MQSLPNSNGAAAGRDFKMKLWDVVAVCLV-LLHTASAFPLPAGKRPPEAPAEDRSLG RRRA-PFALSSDSNMPEDYPDQFDDVMDFIQATIKRLKRSP-DKQMAVLPRRERNRQAA AANPENSRGKGRRGQRGKNRGCVLTAIHLNVTDL-GLGYETKEELIFRYCSGSCDAAE TTYDKILKNLSRN-RRLVSDKVGQACCRPIAFDDDLSFLDDNLVYHIL-RKHSAKRCGCI Human GDNF variant 4 is set forth in SEQ ID NO: 4, MQSLPNSNGAAAGRDFKMKLWDVVAVCLV-LLHTASAFPLPAANMPEDYPDQFDDV MDFIQA-TIKRLKRSPDKQMAVLPRRERNRQAAAANPENSRG-KGRRGQRGKNRGCVL TAIHLNVTDLGLGYETKEELIFRYCSGSCDAAETTY-DKILKNLSRNRRLVSDKVGQAC CRPIAFDDDLS-FLDDNLVYHILRKHSAKRCGCI.

The sequence for human pre-pro GDNF is set forth in SEQ ID NO:5, Met Lys Leu Trp Asp Val Val Ala Val Cys Leu Val Leu Leu His Thr Ala Ser Ala Phe Pro Leu Pro Ala Gly Lys Arg Pro Pro Glu Ala Pro Ala Glu Asp Arg Ser Leu Gly Arg Arg Arg Ala Pro Phe Ala Leu Ser Ser Asp Ser Asn Met Pro Glu Asp Tyr Pro Asp Gln Phe Asp Asp Val Met Asp Phe Ile Gln Ala Thr Ile Lys Arg Leu Lys Arg Ser Pro Asp Lys Gln Met Ala Val Leu Pro Arg Arg Glu Arg Asn Arg Gln Ala Ala Ala Ala Asn Pro Glu Asn Ser Arg Gly Lys Gly Arg Arg Gly Gln Arg Gly Lys Asn Arg Gly Cys Val Leu Thr Ala Ile His Leu Asn Val Thr Asp Leu Gly Leu Gly Tyr Glu Thr Lys Glu Glu Leu Ile Phe Arg Tyr Cys Ser Gly Ser Cys Asp Ala Ala Glu Thr Thr Tyr Asp Lys Ile Leu Lys Asn Leu Ser Arg Asn Arg Arg Leu Val Thr Asp Lys Val Gly Gln Ala Cys Cys Arg Pro Ile Ala Phe Asp Asp Asp Leu Ser Phe Leu Asp Asp Asn Leu Val Tyr His Ile Leu Arg Lys His Ser Ala Lys Arg Cys Gly Cys Ile.

The sequence for Rat pre-pro GDNF is set forth in SEQ ID NO:6, Met Lys Leu Trp Asp Val Val Ala Val Cys Leu Val Leu Leu His Thr Ala Ser Ala Phe Pro Leu Pro Ala Gly Lys Arg Leu Leu Glu Ala Pro Ala Glu Asp His Ser Leu Gly His Arg Arg Val Pro Phe Ala Leu Thr Ser Asp Ser Asn Met Pro Glu Asp Tyr Pro Asp Gln Phe Asp Asp Val Met Asp Phe Ile Gln Ala Thr Ile Lys Arg Leu Lys Arg Ser Pro Asp Lys Gln Ala Ala Ala Leu Pro Arg Arg Glu Arg Asn Arg Gln Ala Ala Ala Ala Ser Pro Glu Asn Ser Arg Gly Lys Gly Arg Arg Gly Gln Arg Gly Lys Asn Arg Gly Cys Val Leu Thr Ala Ile His Leu Asn Val Thr Asp Leu Gly Leu Gly Tyr Glu Thr Lys Glu Glu Leu Ile Phe Arg Tyr Cys Ser Gly Ser Cys Glu Ala Ala Glu Thr Met Tyr Asp Lys Ile Leu Lys Asn Leu Ser Arg Ser Arg Arg Leu Thr Ser Asp Lys Val Gly Gln Ala Cys Cys Arg Pro Val Ala Phe Asp Asp Asp Leu Ser Phe Leu Asp Asp Ser Leu Val Tyr His Ile Leu Arg Lys His Ser Ala Lys Arg Cys Gly Cys Ile.

The sequence for mature human GDNF may be described in SEQ ID NO:7, Ser Pro Asp Lys Gln Met Ala Val Leu Pro Arg Arg Glu Arg Asn Arg Gln Ala Ala Ala Ala Asn Pro Glu Asn Ser Arg Gly Lys Gly Arg Arg Gly Gln Arg Gly Lys Asn Arg Gly Cys Val Leu Thr Ala Ile His Leu Asn Val Thr Asp Leu Gly Leu Gly Tyr Glu Thr Lys Glu Glu Leu Ile Phe Arg Tyr Cys Ser Gly Ser Cys Asp Ala Ala Glu Thr Thr Tyr Asp Lys Ile Leu Lys Asn Leu Ser Arg Asn Arg Arg Leu Val Thr Asp Lys Val Gly Gln Ala Cys Cys Arg Pro Ile Ala Phe Asp Asp Asp Leu Ser Phe Leu Asp Asp Asn Leu Val Tyr His Ile Leu Arg Lys His Ser Ala Lys Arg Cys Gly Cys Ile.

Active variant fragments of GDNF are provided in U.S. Pat. Nos. 7,390,781 and 6,184,200, both hereby incorporated by reference in their entirety. Other contemplated GDNF receptor agonists include active fragments of GDNF such as Met Ser Pro Glu Asn Ser Arg Gly Lys Gly Arg Arg Gly Gln Arg Gly Lys Asn Arg Gly Cys Val Leu Thr Ala Ile His Leu Asn Val Thr Asp Leu Gly Leu Gly Tyr Glu Thr Asn Glu Glu Leu Ile Phe Arg Tyr Cys Ser Gly Ser Cys Asp Ala Ala Glu Thr Thr Tyr Asp Lys Ile Leu Lys Asn Leu Ser Arg Asn Arg Arg Leu Val Thr Asp Lys Val Gly Gln Ala Cys Cys Arg Pro Ile Ala Phe Asp Asp Asp Leu Ser Phe Leu Asp Asp Asn Leu Val Tyr His Ile Leu Arg Lys His Ser Ala Lys Arg Cys Gly Cys Ile (SEQ ID NO:8);

Arg Gly Gln Arg Gly Lys Asn Arg Gly Cys Val Leu Thr Ala Ile His Leu Asn Val Thr Asp Leu Gly Leu Gly Tyr Glu Thr Lys Glu Glu Leu Ile Phe Arg Tyr Cys Ser Gly Ser Cys Asp Ala Ala Glu Thr Thr Tyr Asp Lys Ile Leu Lys Asn Leu Ser Arg Asn Arg Arg Leu Val Thr Asp Lys Val Gly Gln Ala Cys Cys Arg Pro Ile Ala Phe Asp Asp Asp Leu Ser Phe Leu Asp Asn Leu Val Tyr His Ile Leu Arg Lys His Ser Ala Lys Arg Cys Gly Cys Ile (SEQ ID NO:9); and Cys Val Leu Thr Ala Ile His Leu Asn Val Thr Asp Leu Gly Leu Gly Tyr Glu Thr Lys Glu Glu Leu Ile Phe Arg Tyr Cys Ser Gly Ser Cys Asp Ala Ala Glu Thr Thr Tyr Asp Lys Ile Leu Lys Asn Leu Ser Arg Asn Arg Arg Leu Val Thr Asp Lys Val Gly Gln Ala Cys Cys Arg Pro Ile Ala Phe Asp Asp Asp Leu Ser Phe Leu Asp Asp Asn Leu Val Tyr His Ile Leu Arg Lys His Ser Ala Lys Arg Cys Gly Cys (SEQ ID NO:10).

Polypeptides comprising a GDNF sequence active variant or fragment include chimeric proteins. In certain embodiments, the polypeptide is a GDNF fusion protein conjugated to antibody or antibody fragment against the human insulin receptor or against transferrin receptor. See Boado et al., GDNF fusion protein for targeted-drug delivery across the human blood-brain barrier. Biotechnol Bioeng., 2008, 100: 387-396, and Boado et al., Engineering and expression of a chimeric transferrin receptor monoclonal antibody for blood-brain barrier delivery in the mouse. Biotechnol Bioeng., 2009, 102:1251-1258, both hereby incorporated by reference in their entirety. In certain embodiments, the GDNF receptor agonist is not capable of crossing the human blood brain barrier. In certain embodiments, the polypeptide is not conjugated to a protein for transmission across the blood brain barrier.

Preparation GDNF, Variants, Derivatives, Conjugates, and Fragments

A nucleic acid sequence encoding truncated GDNF, or a mature GDNF starting material, can readily be obtained in a variety of ways, including, without limitation, chemical synthesis, cDNA or genomic library screening, expression library screening, and/or PCR amplification of cDNA. These methods and others useful for isolating such nucleic acid sequences are set forth, for example, by Sambrook et al. (Molecular Cloning: A Laboratory Manual, Cold Spring Harbor Laboratory Press, Cold Spring Harbor, N.Y., 1989), by Ausubel et al., eds (Current Protocols in Molecular Biology, Current Protocols Press, 1994), and by Berger and Kimmel (Methods in Enzymology: Guide to Molecular Cloning Techniques, vol. 152, Academic Press, Inc., San Diego, Calif., 1987). Preferred nucleic acid sequences encoding GDNF are mammalian sequences.

Chemical synthesis of a nucleic acid sequence which encodes a polypeptide can also be accomplished using methods well known in the art, such as those set forth by Engels et al. (Angew. Chem. Intl. Ed., 28:716-734, 1989). These methods include, inter alia, the phosphotriester, phosphoramidite and H-phosphonate methods of nucleic acid sequence synthesis. The nucleic acid sequence encoding the truncated GDNF protein will be several hundred base pairs (bp) or nucleotides in length. Large nucleic acid sequences, for example those larger than about 100 nucleotides in length, can be synthesized as several fragments. The fragments can then be ligated together to form a nucleic acid sequence encoding truncated GDNF protein. A preferred method is polymer-supported synthesis using standard phosphoramidite chemistry.

Alternatively, a suitable nucleic acid sequence may be obtained by screening an appropriate cDNA library (i.e., a library prepared from one or more tissue source(s) believed to express the protein) or a genomic library (a library prepared from total genomic DNA). The source of the cDNA library is typically a tissue from any species that is believed to express GDNF in reasonable quantities. The source of the genomic library may be any tissue or tissues from any mammalian or other species believed to harbor a gene encoding GDNF or a GDNF homologue. The library can be screened for the presence of the GDNF cDNA/gene using one or more nucleic acid probes (oligonucleotides, cDNA or genomic DNA fragments that possess an acceptable level of homology to the GDNF or GDNF homologue cDNA or gene to be cloned) that will hybridize selectively with GDNF or GDNF homologue cDNA(s) or gene(s) present in the library. The probes typically used for such library screening usually encode a small region of the GDNF DNA sequence from the same or a similar species as the species from which the library was prepared. Alternatively, the probes may be degenerate.

Library screening is typically accomplished by annealing the oligonucleotide probe or cDNA to the clones in the library under conditions of stringency that prevent non-specific binding but permit binding of those clones that have a significant level of homology with the probe or primer. Typical hybridization and washing stringency conditions depend in part on the size (i.e., number of nucleotides in length) of the cDNA or oligonucleotide probe, and whether the probe is degenerate. The probability of obtaining a clone(s) is also considered in designing the hybridization solution (i.e., whether a cDNA or genomic library is being screened; if it is a cDNA library, the probability that the cDNA of interest is present at a high level).

Another suitable method for obtaining a nucleic acid sequence encoding a polypeptide is the polymerase chain reaction (PCR). In this method, poly(A)+RNA or total RNA is extracted from a tissue that expresses GDNF. cDNA is then prepared from the RNA using the enzyme reverse transcriptase. Two primers, typically complementary to two separate regions of the GDNF cDNA (oligonucleotides), are then added to the cDNA along with a polymerase such as Taq polymerase, and the polymerase amplifies the cDNA region between the two primers.

The cDNA or genomic DNA encoding a polypeptide is inserted into a vector for further cloning (amplification of the DNA) or for expression. Suitable vectors are commercially available, or the vector may be specially constructed. The selection or construction of the appropriate vector will depend on 1) whether it is to be used for DNA amplification or for DNA expression, 2) the size of the DNA to be inserted into the vector, and 3) the host cell (e.g., mammalian, insect, yeast, fungal, plant or bacterial cells) to be transformed with the vector. Each vector contains various components depending on its function (amplification of DNA or expression of DNA) and its compatibility with the intended host cell. The vector components generally include, but are not limited to, one or more of the following: a signal sequence, an origin of replication, one or more selection or marker genes, enhancer elements, promoters, a transcription termination sequence, and the like. These components may be obtained from natural sources or synthesized by known procedures. The vectors of the present invention involve a nucleic acid sequence which encodes the polypeptide of interest operatively linked to one or more of the following expression control or regulatory sequences capable of directing, controlling or otherwise effecting the expression of the polypeptide by a selected host cell.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and occasionally 3' untranslated regions of eukaryotic DNAs or cDNAs. These regions contain nucleotide segments transcribed as polyadenylated fragments in the untranslated portion of the mRNA encoding polypeptide.

The construction of suitable vectors containing one or more of the above-listed components together with the desired polypeptide coding sequence is accomplished by standard ligation techniques. Isolated plasmids or DNA fragments are cleaved, tailored, and religated in the desired order to generate the plasmids required. To confirm that the correct sequences have been constructed, the ligation mixtures may be used to transform *E. coli*, and successful transformants may be selected by known techniques, such as ampicillin or tetracycline resistance as described above. Plasmids from the transformants are then prepared, analyzed by restriction endonuclease digestion, and/or sequenced to confirm the presence of the desired construct.

Host cells (e.g., bacterial, mammalian, insect, yeast, or plant cells) transformed with nucleic acid sequences for use in expressing a recombinant polypeptides are also provided by the present disclosure. The transformed host cell is cultured under appropriate conditions permitting the expression of the nucleic acid sequence. The selection of suitable host cells and methods for transformation, culture, amplification, screening and product production and purification are well known in the art. See for example, Gething and Sambrook, Nature 293: 620-625 (1981), or alternatively, Kaufman et al., Mol. Cell. Biol., 5 (7): 1750-1759 (1985) or Howley et al., U.S. Pat. No. 4,419,446. Truncated GDNF may be expressed in *E. coli* in accordance with the description of Lin et al. (U.S. patent application Ser. No. 07/855,413) which involved the expression of mature GDNF. Other exemplary materials and methods are discussed in further detail below. The transformed host cell is cultured in a suitable medium, and the expressed factor is then optionally recovered, isolated and purified from the culture medium (or from the cell, if expressed intracellularly) by an appropriate means known to those skilled in the art.

Transformed cells used to produce polypeptides of the present invention are cultured in suitable media. The media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamicin), trace elements (defined as inorganic compounds usually present at final concentrations in the micromolar range), and glucose or other energy source. Other supplements may also be included, at appropriate concentrations, as will be appreciated by those skilled in the art. Suitable culture conditions, such as temperature, pH, and the like, are also well known to those skilled in the art for use with the selected host cells.

Chemically modified derivatives of GDNF, variants or truncated GDNF variants may be prepared by one skilled in the art given the disclosures herein. The chemical moieties most suitable for derivatization of polypeptide include water soluble polymers. A water soluble polymer is desirable because the protein to which it is attached does not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically, and if so, the desired dosage, circulation time, resistance to proteolysis, and other considerations. The effectiveness of the derivatization may be ascertained by administering the derivative, in the desired form (i.e., by osmotic pump, or, more preferably, by injection or infusion, or further formulated for oral, pulmonary or other delivery routes), and determining its effectiveness.

Suitable water soluble polymers include, but are not limited to, polyethylene glycol (PEG), copolymers of ethylene glycol/propylene glycol, monomethoxy-polyethylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), poly(n-vinyl pyrrolidone)polyethylene glycol, polypropylene glycol homopolymers, polypropylene oxide/ethylene oxide co-polymers, polyoxyethylated polyols (e.g., glycerol), polyethylene glycol propionaldehyde, and mixtures thereof. As used herein, polyethylene glycol is meant to encompass any of the forms of PEG that have been used to derivatize other proteins, such as mono-(C1-C10) alkoxy- or aryloxy-polyethylene glycol. Polyethylene glycol propionaldehyde may have advantages in manufacturing due to its stability in water. The polymer may be of any molecular weight, and may be branched or unbranched.

The present disclosure particularly relates to GDNF protein variant or truncated products involving truncated GDNF protein linked to at least one PEG molecule. In another aspect, the present disclosure relates to truncated GDNF protein attached to at least one PEG molecule via an acyl or alkyl linkage.

Pegylation may be carried out by any of the pegylation reactions known in the art. See, for example: Focus on Growth Factors 3(2): 4-10 (1992); EP 0 154 316; EP 0 401384; and Malik et al., Exp. Hematol. 20: 1028-1035 (1992) (reporting pegylation of GM-CSF using tresyl chloride). Preferably, the pegylation is carried out via an acylation reaction or an alkylation reaction with a reactive water soluble polymer. These preferred means for derivatization are discussed in greater detail, below. For the acylation reactions, the polymer(s) selected preferably have a single reactive ester group. For the reductive alkylation reactions, the polymer(s) selected preferably have a single reactive aldehyde group. In addition, the selected polymer may be modified to have a single reactive group, such as an active ester for acylation or an aldehyde for alkylation, so that the degree of polymerization may be controlled. Generally, the water soluble polymer will not be selected from naturally-occurring glycosyl residues since these are usually made more conveniently by mammalian recombinant expression systems.

In the present disclosure, pegylation by acylation generally involves reacting an active ester derivative of polyethylene glycol with a truncated GDNF protein. Any known or subsequently discovered reactive PEG molecule may be used to carry out the pegylation process. A preferred activated PEG ester is PEG esterified to N-hydroxysuccinimide ("NETS"). As used herein, "acylation" is contemplated to included without limitation the following types of linkages between a truncated GDNF protein and a water soluble polymer such as PEG: amide, carbamate, urethane, and the like. See Bioconjugate Chem. 5: 133-140 (1994). Reaction conditions may be selected from any of those known in the pegylation art or those subsequently developed, but should avoid or limit exposure to reaction conditions such as temperatures, solvents, and pH levels that would inactivate the truncated GDNF protein to be modified.

Pegylation by acylation will generally result in a poly-pegylated truncated GDNF protein, wherein the lysine amino groups are pegylated via an acyl linking group. Preferably, the connecting linkage will be an amide. Also preferably, the resulting product will be substantially only (e.g., 95%) mono-, di- or tri-pegylated. However, some conjugates with higher degrees of pegylation may be formed in amounts depending on the specific reaction conditions used. If desired, more purified pegylated conjugates may be prepared from the mixture by standard purification techniques, including, among others, dialysis, salting-out, ultra-filtration, ion-exchange chromatography, gel filtration chromatography and electrophoresis.

In the present disclosure, pegylation by alkylation generally involves reacting a terminal aldehyde derivative of PEG with a truncated GDNF protein in the presence of a reducing agent. Pegylation by alkylation can also result in a poly-pegylated truncated GDNF protein. In addition, one can manipulate the reaction conditions to favor pegylation substantially only at the .alpha.-amino group of the N-terminus of the protein (i.e., a mono-pegylated species). In either case of mono-pegylation or polypegylation, the PEG groups are preferably attached to the protein via a —$CH_2$—NH— group. With particular reference to the —$CH_2$— group, this type of linkage is referred to herein as an "alkyl" linkage.

Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group-containing polymer is achieved. For example, one may selectively N-terminally pegylate the protein by performing the reaction at a pH which allows one to take advantage of the pKa differences between the amino group of the lysine residues and that of the amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer preferably has a single reactive aldehyde for coupling to the protein. Polyethylene glycol propionaldehyde, containing a single reactive aldehyde, may be used.

The present disclosure includes pegylated GDNF, variant, or truncated proteins, wherein the PEG group(s) is (are) attached via acyl or alkyl groups. As discussed above, such truncated GDNF protein products may be mono-pegylated or poly-pegylated (e.g., containing 2-6, preferably 2-5, PEG groups). The PEG groups are generally attached to the protein at the amino groups of amino acids, but it is also contemplated that the PEG groups could be attached to any reactive group of to the protein, which is sufficiently reactive to become attached to a PEG group under suitable reaction conditions. Thus, polyethylene glycol may be covalently bound to a protein via a reactive group, such as, a free amino or carboxyl group. Reactive groups are those to which an activated PEG molecule may be bound. The amino acid residues having a free amino group may include lysine residues and the N-terminal amino acid residue. Those having a free carboxyl group may include aspartic acid residues, glutamic acid residues, and the C-terminal amino acid residue. Sulfhydryl groups may also be used as a reactive group for attaching PEG molecule(s). For therapeutic purposes, attachment at an amino group, such as attachment at the N-terminus or lysine group is typically preferred. Attachment at residues important for receptor binding should be avoided if receptor binding is desired.

In one aspect, the present disclosure provides for a substantially homogeneous preparation of mono-polymer/protein conjugate wherein a polymer molecule has been attached substantially only (i.e., 95%) in a single location. More specifically, if PEG is used, the present disclosure also provides for pegylated a truncated GDNF protein lacking possibly antigenic linking groups, and having the PEG molecule directly coupled to the truncated GDNF protein.

For reductive alkylation, the reducing agent should be stable in aqueous solution and preferably be able to reduce only the Schiff base formed in the initial process of reductive alkylation. Exemplary reducing agents may be selected from the group consisting of sodium borohydride, sodium cyanoborohydride, dimethylamine borane, trimethylamine borane and pyridine borane. A particularly preferred reducing agent is sodium cyanoborohydride. Other reaction parameters, such as solvent, reaction times, temperatures, etc., and means of purification of products, can be determined case-by-case based on commonly available information relating to derivatization of proteins with water soluble polymers.

Formulations

In certain embodiments, the disclosure contemplates oral, systemically, or peripherally administering a pharmaceutical composition comprising a GDNF receptor agonist for reducing or preventing weight gain. In certain embodiments, administration excludes intracranial delivery.

"Systemic" administration refers to any method of delivery into the body's general blood or lymphatic circulation. The typical, but not only, method of systemic delivery is intravenous injection. Systemic delivery may also include peripheral administration simultaneously at one or more sites on or within the body.

"Peripheral" administration refers to any method of delivery targeting a particular site within the body. This includes, but is not limited to, delivery via transdermal patch, subcutaneous injection, oral, ocular, rectal, intramuscular, or intranasal routes. The typical, but not only, target site within the body is adipose tissue. Peripheral administration may result in eventual systemic delivery.

Generally, for pharmaceutical use, the compositions may be formulated as a pharmaceutical preparation comprising at least one GDNF receptor agonist and at least one pharmaceutically acceptable carrier, diluent or excipient and/or adjuvant, and optionally one or more further pharmaceutically active compositions.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, e.g. about 10, 25, 50, 100, 200, 300 or 400 mg per unit dosage.

The compositions can be administered by a variety of routes including the oral, ocular, rectal, transdermal, subcutaneous, intravenous, intramuscular or intranasal routes, depending mainly on the specific preparation used. In certain embodiments, the disclose contemplates intravenously-delivered IgG-GDNF fusion protein capable of passing through the blood-brain barrier. See Fu, et al. Intravenous treatment of experimental Parkinson's disease in the mouse with an IgG-GDNF fusion protein that penetrates the blood-brain barrier. Brain Res. 2010 Sep. 17; 1352:208-13, hereby incorporated by reference in its entirety.

The embodiments will generally be administered in an "effective amount", by which is meant any amount of a composition that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

For an oral administration form, the composition can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compositions of the disclosure or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous or intravenous administration, the compositions, if desired with the substances customary therefore such as solubilizers, emulsifiers or further auxiliaries are brought into solution, suspension, or emulsion. The compositions can also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compositions with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethyl methacrylate)); carboxypolymethylene (for example Carbopol™); carbomer; polyvinyl pyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxy methylcellulose (HMC), hydroxyethylcellulose (HEC), hydroxypropylcellulose (HPC), methylcellulose (MC), ethylcellulose (EC), carboxyethylcellulose (CEC), ethylhydroxy ethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxy groups and hydroxypropoxy groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein delivery systems. Proteins can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol) to proteins (pegylation) to increase the in vivo half-life of circulating therapeutic proteins.

Combination Therapies

In certain embodiments, the disclosure relates to the use of GDNF agonist for the treatment or prevention of weight gain by orally or systemically administering a GDNF agonist in combination with another weight loss therapeutic, insulin resistance therapeutic, or a metabolic syndrome therapeutic.

As used herein, the term "combined with" when used to describe the administration of GDNF and any additional treatment(s), e.g. weight loss therapeutic, means that the additional treatment(s) may be administered prior to, together with, or after the administration of GDNF, or a combination thereof.

As used herein, the term "weight loss therapeutic" refers to any therapy for managing body weight. This includes pharmaceuticals, bariatric surgery, changes in diet, exercise regimens, and any combination thereof. Such pharmaceuticals include, but are not limited to, dinitrophenol, exendin-4, human growth hormone, lorcaserin, metformin or other GLP-1 receptor agonists, orlistat, phentermine, pramlintide, rimonabant, sibutramine, sitagliptin and other DPP-IV inhibitors, and ZGN-433. Bariatric surgery may include, but is not limited to, biliopancreatic diversion, use of an endoluminal sleeve, use of an intragastric balloon, gastric banding, gastric bypass, gastric plication, sleeve gastrectomy with or without a duodenal switch, and vertical banded gastroplasty.

As used herein, the term "insulin resistance therapeutic" refers to any therapy for managing insulin resistance. This includes pharmaceuticals, bariatric surgery, changes in diet, exercise regimens, and any combination thereof. Such pharmaceuticals include, but are not limited to, chromium, exendin-4, metformin, thiazolidinediones, and/or vanadium. Such bariatric surgery may include, but is not limited to, biliopancreatic diversion, use of an endoluminal sleeve, use of an intragastric balloon, gastric banding, gastric bypass, gastric plication, sleeve gastrectomy with or without a duodenal switch, and vertical banded gastroplasty.

As used herein, the term "metabolic syndrome therapeutic" refers to any therapy for managing metabolic syndrome. Such therapy includes, but is not limited to, ACE inhibitors, changes in diet, cholesterol-adjusting pharmaceuticals, diuretics, and exercise. "Metabolic syndrome therapeutic" may also include any of the insulin resistance and/or weight loss therapeutics listed above.

Terms

As used herein, the term "obese", when used in the context of treating weight gain, means obese according to a classification system of body weight. Such systems include, but are not limited to, the body mass index (BMI), BMI prime, or equivalents (e.g. some organizations or countries may use a different threshold or designation of obesity). BMI, for example, is an analytical tool used to compare a person's height with their weight, as a rough measure of adiposity. BMI is calculated by dividing a person's mass (kg) by the height squared ($m^2$). An individual is classified as obese, when their BMI value is greater than or equal to 30 ($kg/m^2$). The term "obese" may refer to morbid obesity (i.e. BMI greater than or equal to 40), childhood obesity, and any other designation of obesity in which the subject's BMI is greater than or equal to 30.

As used herein, the term "overweight", when used in the context of treating weight gain, means overweight according to a classification system of body weight, as described herein. An individual is classified as overweight, per BMI for example, when their BMI value is equal to or greater than 25.

As used herein, the term "normal weight", when used in the context of treating weight gain, means normal weight according to a classification system of body weight, as described above. An individual is classified as normal weight, per BMI for example, when their BMI value is less than 25 but greater than or equal to 20.

As used herein, the term "derivative", when used in the context of a peptide or polypeptide, means a peptide or polypeptide different other than in primary structure (amino acids and amino acid analogs). By way of illustration, derivatives may differ by being glycosylated, one form of post-translational modification. For example, peptides or polypeptides may exhibit glycosylation patterns due to expression in heterologous systems. If at least one biological activity is retained, then these peptides or polypeptides are derivatives according to the disclosure. Other derivatives include, but are not limited to, fusion peptides or fusion polypeptides having a covalently modified N- or C-terminus, PEGylated peptides or polypeptides, peptides or polypeptides associated with lipid moieties, alkylated peptides or polypeptides, peptides or polypeptides linked via an amino acid side-chain functional group to other peptides, polypeptides or chemicals, and additional modifications as would be understood in the art.

As used herein, the term "variant", when used in the context of a peptide or polypeptide, means a peptide or polypeptide that differs in amino acid sequence by the insertion, deletion, or conservative substitution of amino acids, but retain at least one biological activity. For purposes of this disclosure, "biological activity" includes, but is not limited to, the ability to be bound by a specific antibody. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. The hydropathic index of an amino acid is based on a consideration of its hydrophobicity and charge. It is known in the art that amino acids of similar hydropathic indexes can be substituted and still retains protein function. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. See, e.g., U.S. Pat. No. 4,554,101. Substitution of amino acids having similar hydrophilicity values can result in peptides retaining biological activity, for example immunogenicity, as is understood in the art. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

The term "homolog" or "homologous" when used in reference to a polypeptide refers to a high degree of sequence identity between two polypeptides, or to a high degree of similarity between the three-dimensional structures or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

"Sequence identity" refers to a measure of relatedness between two or more nucleic acids or polypeptides/proteins, and is given as a percentage with reference to the total comparison length. The identity calculation takes into account those nucleotide or amino acid residues that are identical and in the same relative positions in their respective larger sequences. Optimal alignment of sequences for aligning a comparison window may be conducted by the local homology algorithm of Smith and Waterman (Smith and Waterman, Adv. Appl. Math. 2: 482 (1981)) by the homology alignment algorithm of Needleman and Wunsch (Needleman and Wunsch, J. Mol. Biol. 48:443 (1970)), by the search for similarity method of Pearson and Lipman (Pearson and Lipman, Proc. Natl. Acad. Sci. (U.S.) 85:2444 (1988)), and by computerized implementations of these algorithms using standard default parameters.

The term "ortholog" refers to the equivalent embodiment in a non-human species. Rat GDNF, for example, is an ortholog of human GDNF.

The terms "treatment" or "treating" include any desirable effect on the symptoms or pathology of a disease or condition, and may include even minimal reductions in one or more measurable markers of the disease or condition being treated. "Treatment" does not necessarily indicate complete eradication or cure of the disease or condition, or associated symptoms thereof. The subject receiving this treatment is any animal in need, including primates, in particular humans, and other mammals such as equines, cattle, swine and sheep; and poultry and pets in general.

EXPERIMENTAL

Figure 1B:
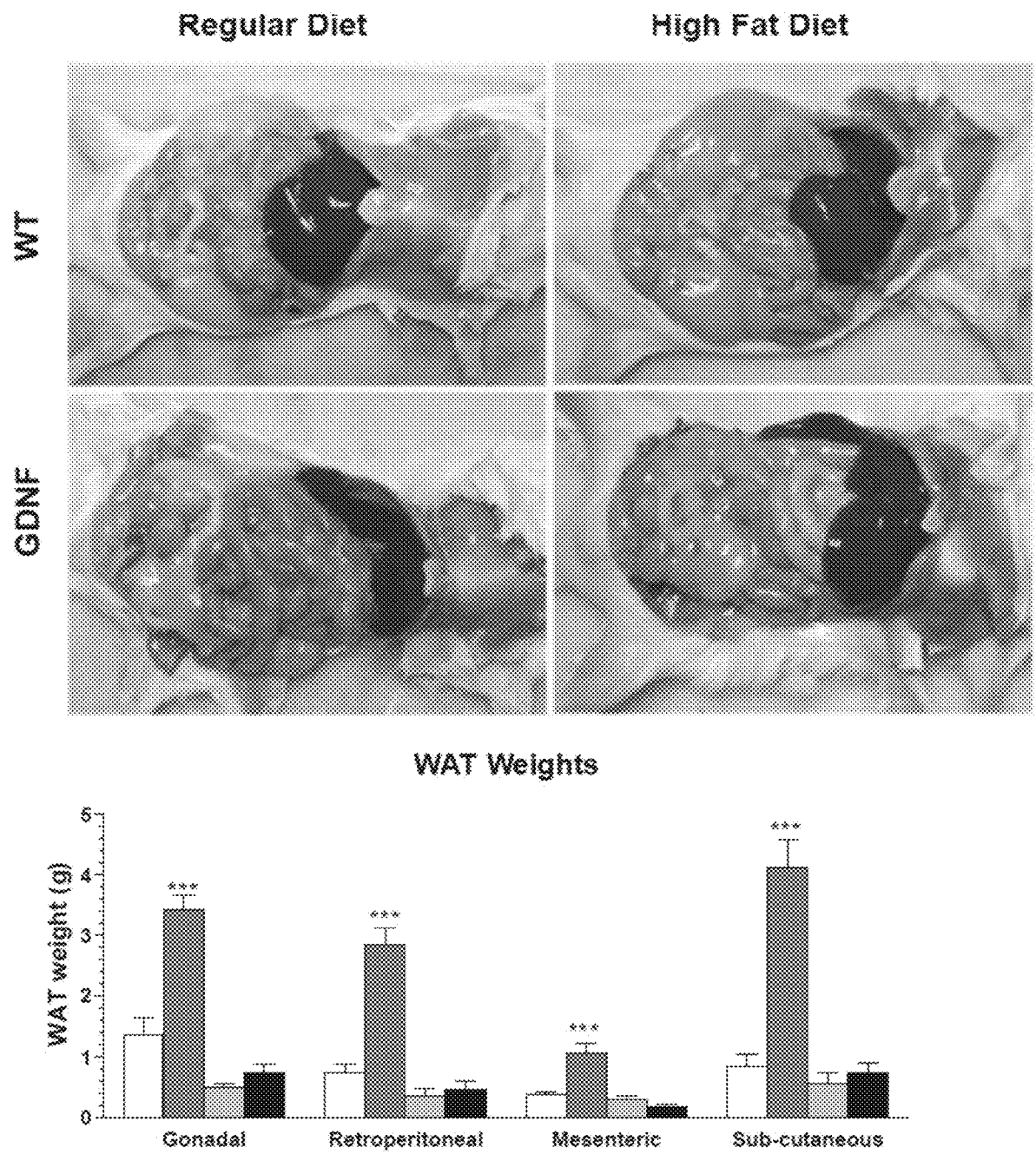
FIG. 1B shows representative images showing WAT fat deposition and comparison of WAT fat weights.
Figure 1C:
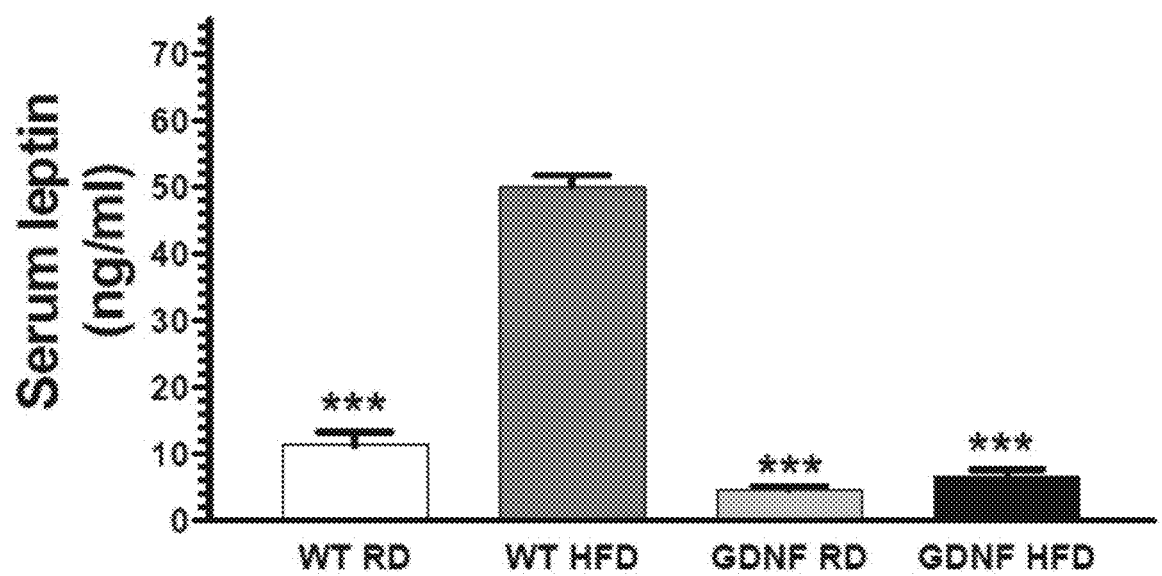
FIG. 1C shows data on serum leptin levels.
Figure 1D:
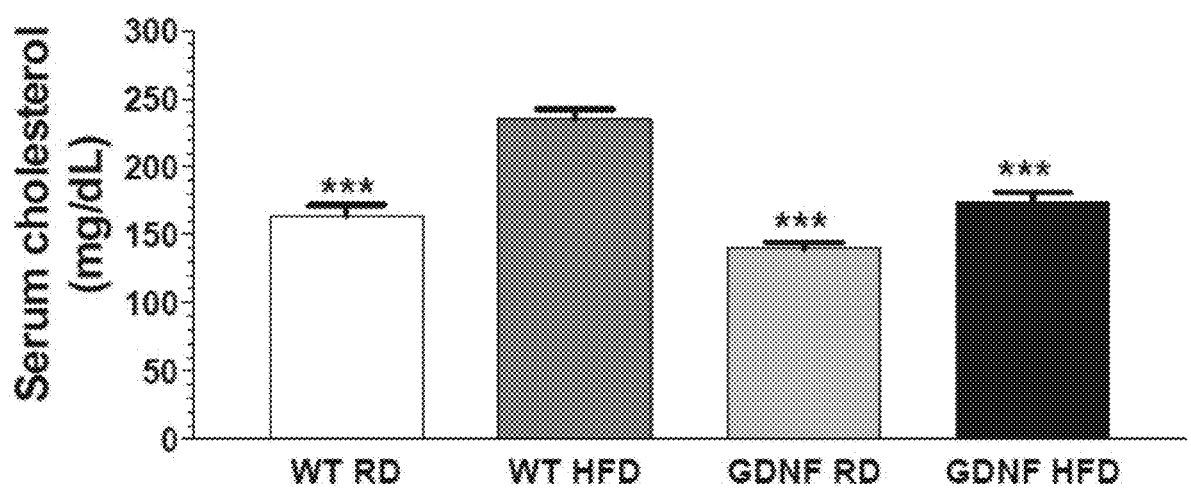
FIG. 1D shows data on serum cholesterol levels.
Figure 1E:
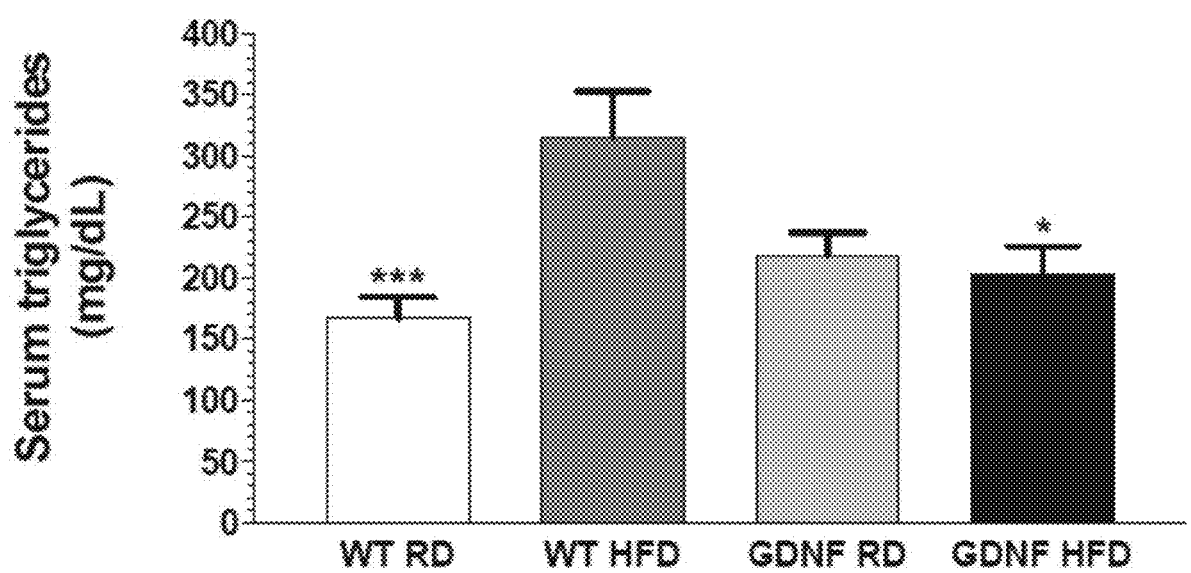
FIG. 1E shows data on serum triglyceride levels of male WT and GDNF-tg mice fed a regular diet (RD) or HFD for 11 weeks. Data presented are means+SE. ***, $P<0.001$; *, $P<0.05$, compared to WT HFD mice (n=5-9 mice per group).

GDNF-tg mice are protected against high-fat diet-induced obesity, hyperleptinemia, hyperlipidemia and hypertriglyceridemia GDNF-tg mice have higher GDNF expression in several tissues including the islets, white adipose tissue (WAT) and the central nervous system than their WT littermates. They also have significantly lower birth weights than WT littermates, but higher growth rates during the first 6 weeks. For this study, 5-6 weeks old age-matched WT and GDNF-tg male mice were fed a regular rodent diet (6.2% fat; 18% cal from fat/58% from carbohydrates) or a high fat diet (34.3% fat; 60% cal from fat/22% from carbohydrates) for 11 weeks and weighed once weekly. GDNF-tg mice fed the HFD diet and those fed the regular diet had similar starting weights and showed similar slow weekly increases the entire study period (FIG. 1A). WT mice fed the high fat diet and those fed the regular diet had similar starting weights too, but from the 4th week onwards WT mice fed the HFD weighed significantly more than WT mice fed the regular diet (FIG. 1A). Comparison of the body weight curves using linear regression analyses showed that WT mice fed the HFD experienced significantly faster (P<0.001) weight gain and after 11 weeks on the diet had gained more weight than WT and GDNF-tg mice fed the regular diet as well as GDNF-tg mice fed the HFD (FIG. 1A). Examination of WAT for fat deposition showed that GDNF-tg mice after feeding on the HFD for 11 weeks had similar amounts of gonadal, retroperitoneal, mesenteric and subcutaneous fat as WT and GDNF-tg mice fed the regular diet, but significantly less (P<0.001) than WT mice fed the HFD (FIG. 1B). In line with a protective role for GDNF against HFD-induced obesity, serum leptin (FIG. 1C), cholesterol (FIG. 1D) and triglyceride (FIG. 1E) levels of GDNF-tg mice fed the HFD for 11 weeks were similar to those of GDNF-tg and WT mice fed the regular diet, but significantly (P<0.001) lower than those of WT mice fed the HFD.

GDNF-Tg Mice have Enhanced Energy Expenditure

Figure 6A:
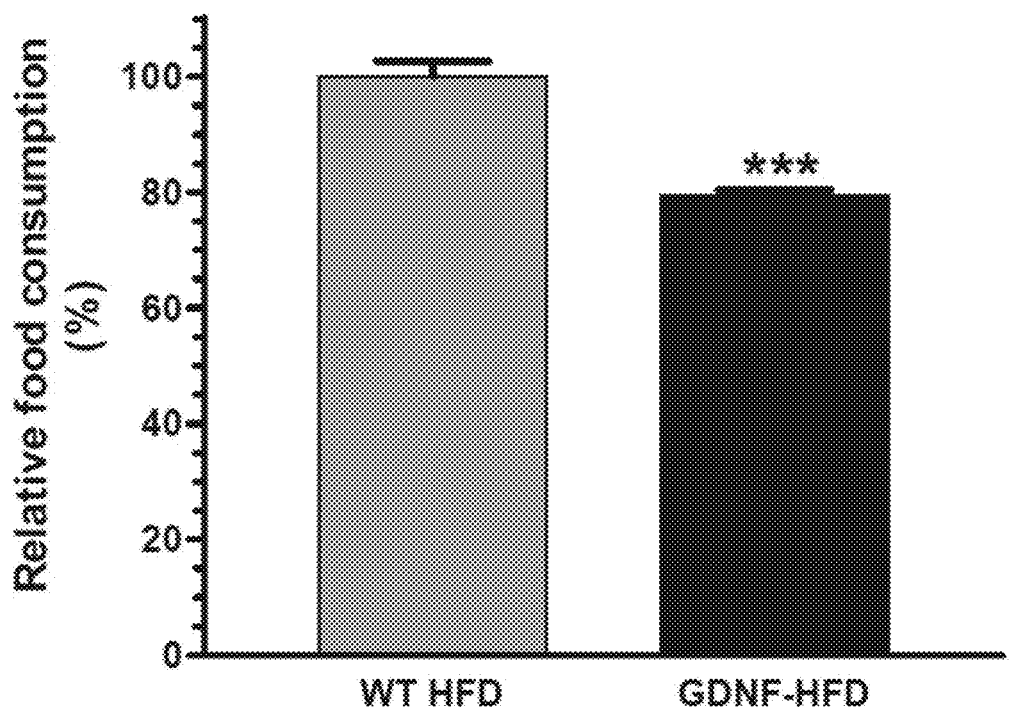
FIG. 6A shows data indicating show data indicating GDNF-tg and WT mice have similar food intake based on relative daily food consumption.
Figure 6B:
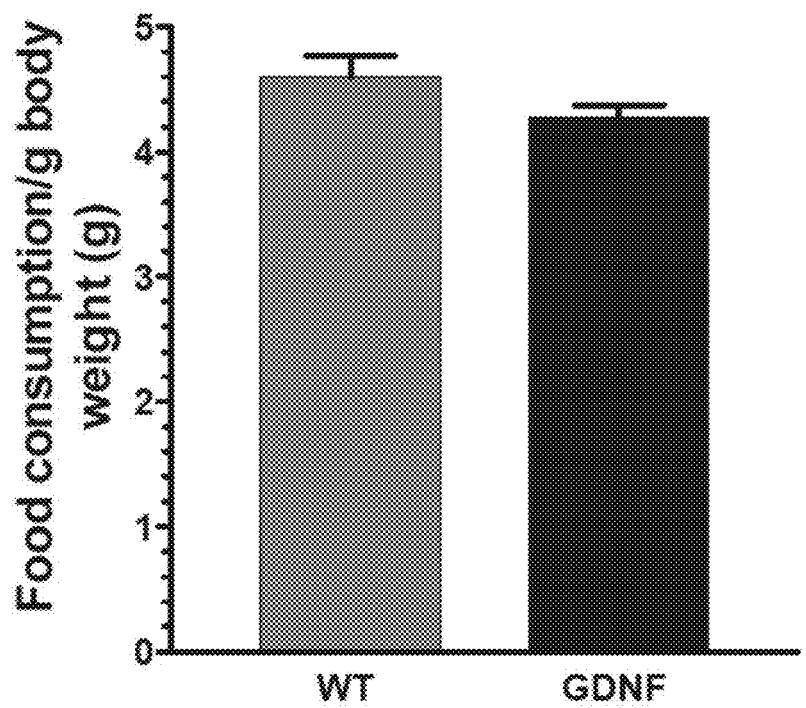
FIG. 6B shows data on adjusted daily food consumption of GDNF-tg and WT mice fed ad libitum a HFD for 14 days.
Figure 6C:
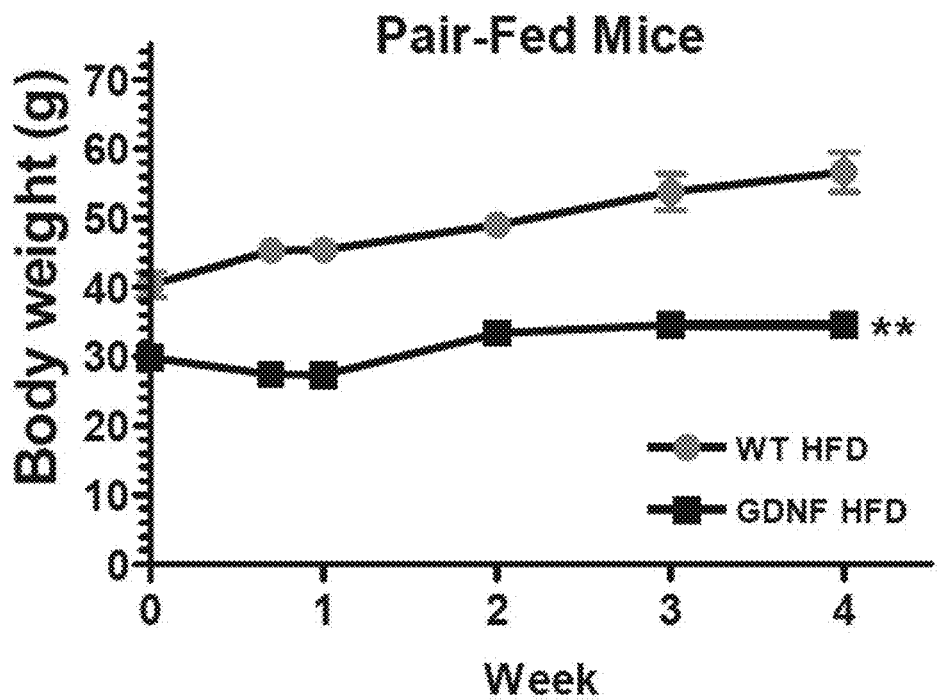
FIG. 6C shows data on body weights for GDNF-tg and WT mice pair-fed a HFD for 4 weeks.
Figure 6D:
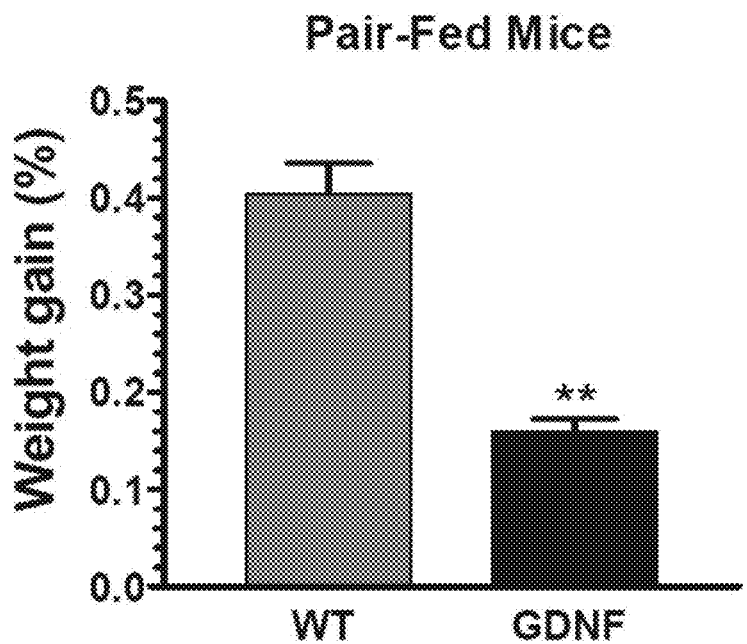
FIG. 6D shows data on weight gain for GDNF-tg and WT mice pair-fed a HFD for 4 weeks.
Figure 7A:
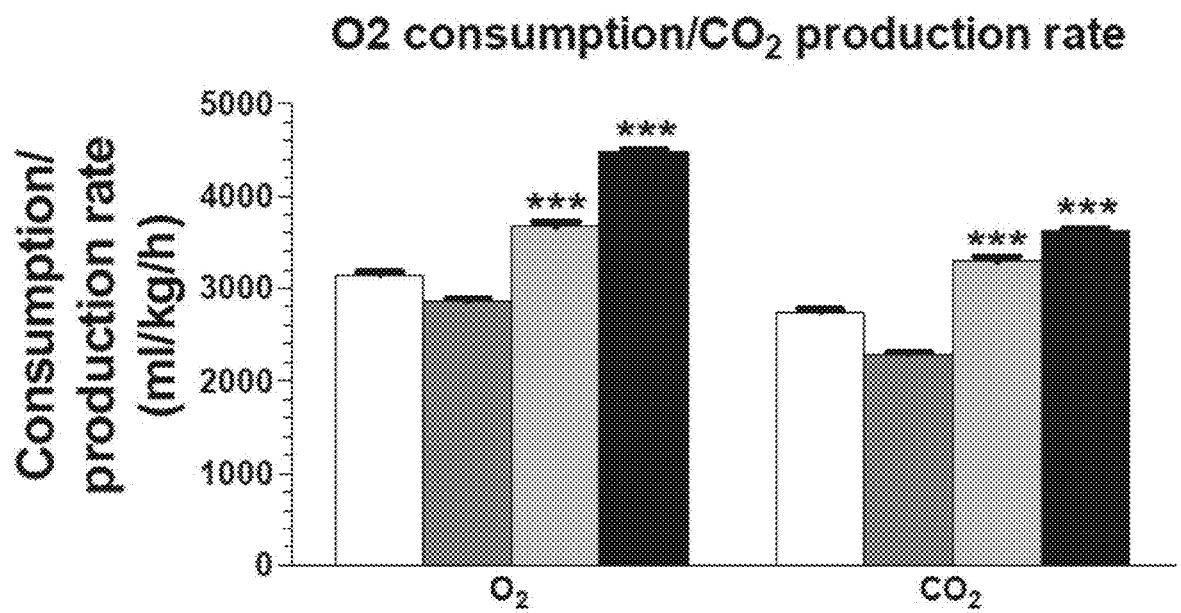
FIG. 7A shows data indicating GDNF-tg mice have higher energy expenditure based on oxygen consumption and carbon dioxide release.
Figure 7B:
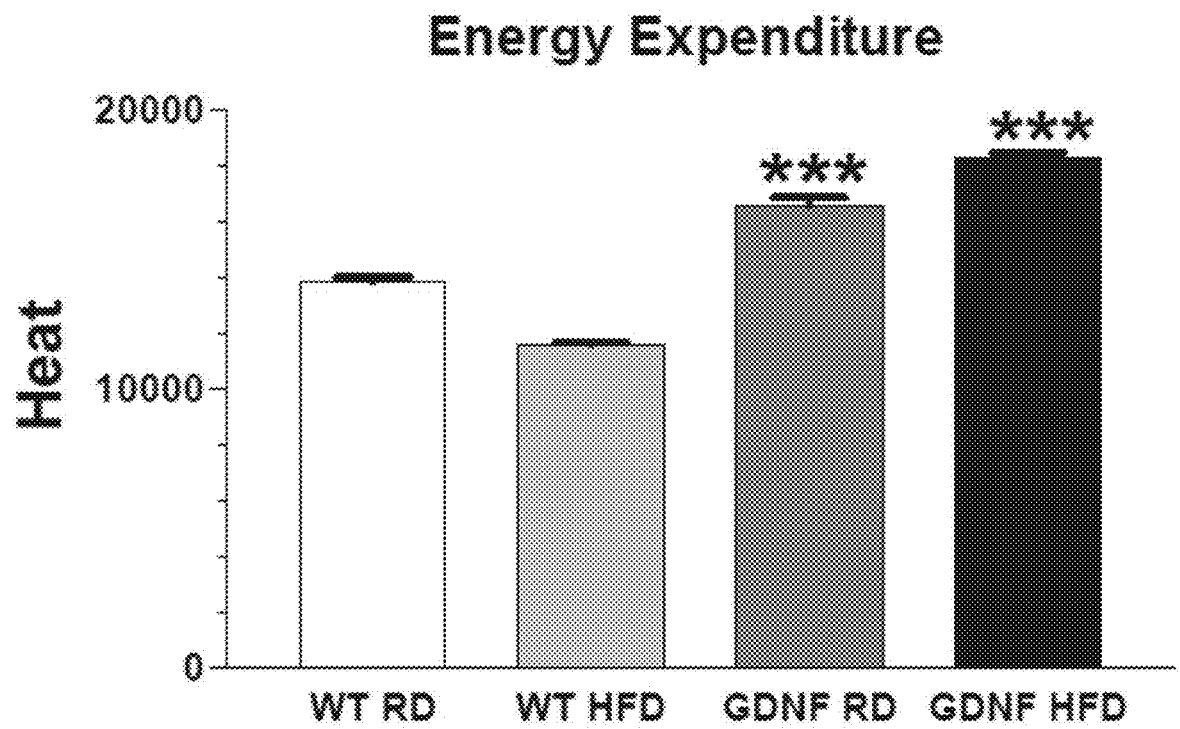
FIG. 7B shows data on energy expenditure.
Figure 7C:
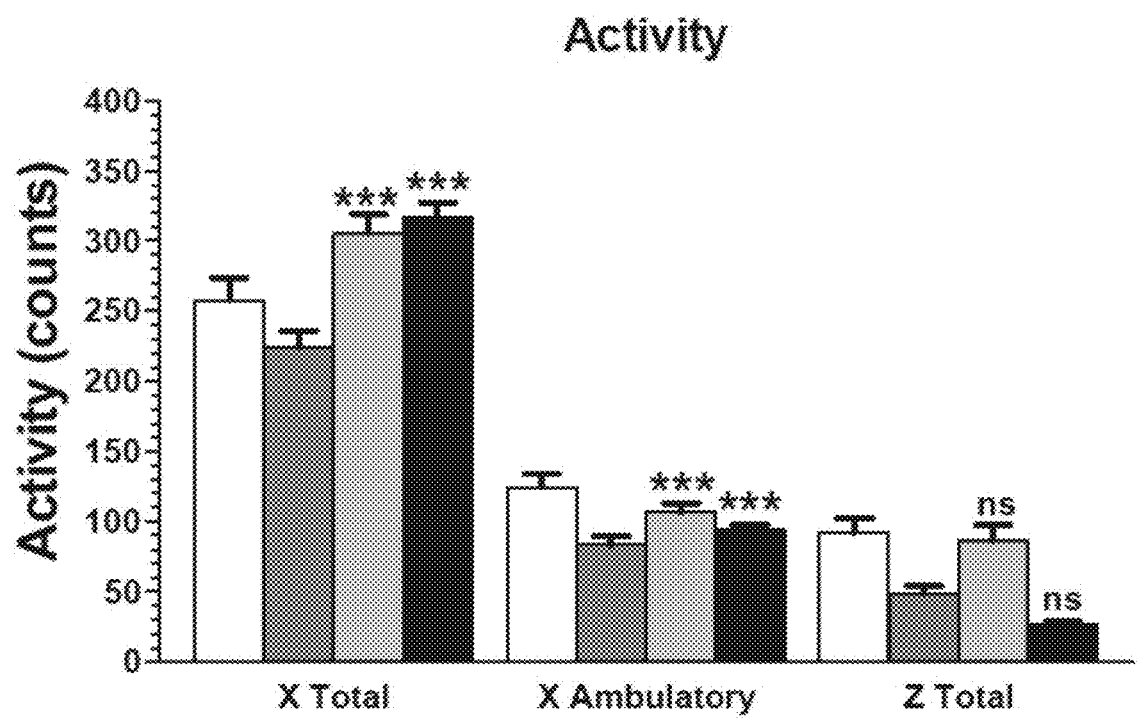
FIG. 7C shows data on activity in male WT and GDNF transgenic mice fed a regular diet or HFD for 11 weeks.

To rule out a role for differences in food intake in the differences in weight gain, food consumption was monitored for 4 weeks in individually caged WT and GDNF-tg mice fed a HFD. While average daily food consumption for WT mice was significantly higher (P<0.01) than that for GDNF-tg mice (FIG. 6A), when adjusted for mice weights there were no significant differences observed between the two groups (FIG. 6B). To explore this further, individually caged WT and GDNF-tg mice littermates were pair-fed a HFD for 4 weeks and weight gain monitored. Even after being daily fed the same amount of food eaten by GDNF-tg mice, WT mice gained significantly (P<0.01) more weight than GDNF-tg mice (FIG. 6C). The effects of GDNF on metabolism was examined using a comprehensive laboratory animal monitoring system (CLAMS). GDNF-tg mice fed the HFD diet as well as those fed the regular diet had significantly (P<0.001) higher oxygen consumption and carbon dioxide release and increased energy expenditure than WT mice fed the HFD diet and those fed the regular diet (FIG. 7A-7B) indicating that protection against HFD-induced obesity in GDNF-tg mice might involve increased energy expenditure. Indeed, assessment of activity showed that both groups of GDNF mice were significantly (P<0.001) more active than the two groups of WT mice.

Figure 2A:
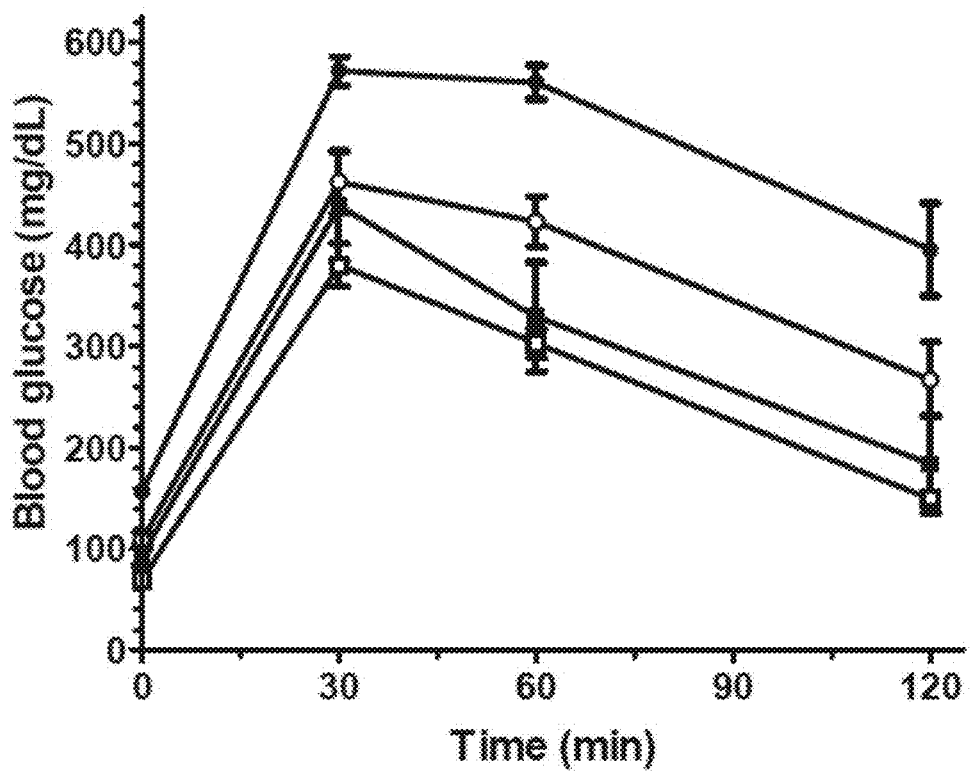
FIG. 2A shows data indicating GDNF-tg mice resist high-fat diet-induced glucose intolerance and insulin resistance. Glucose tolerance test and area under the curve.
Figure 2A:
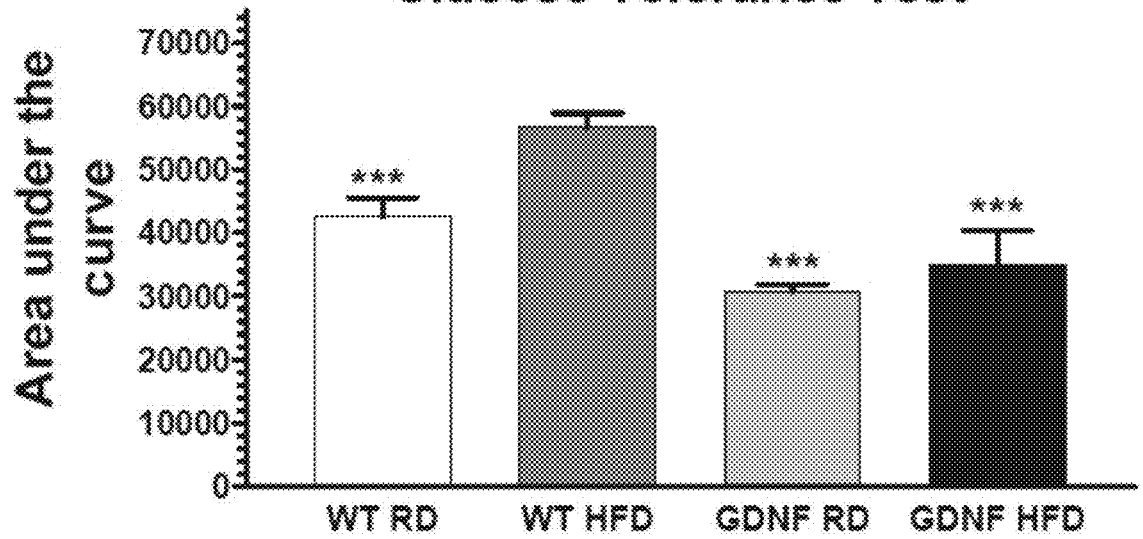
Figure 2B:
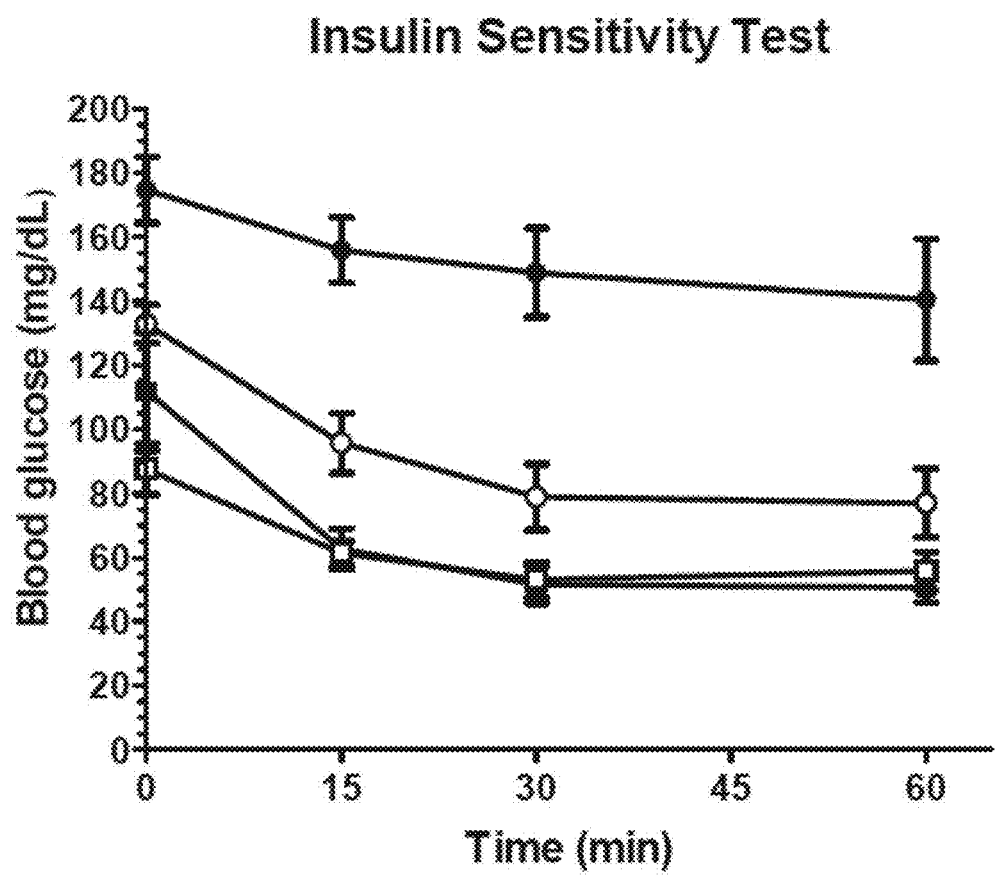
FIG. 2B shows data on insulin sensitivity test and area under the curve in male WT and GDNF transgenic mice fed a regular diet or HFD for 10 weeks.
Figure 2B:
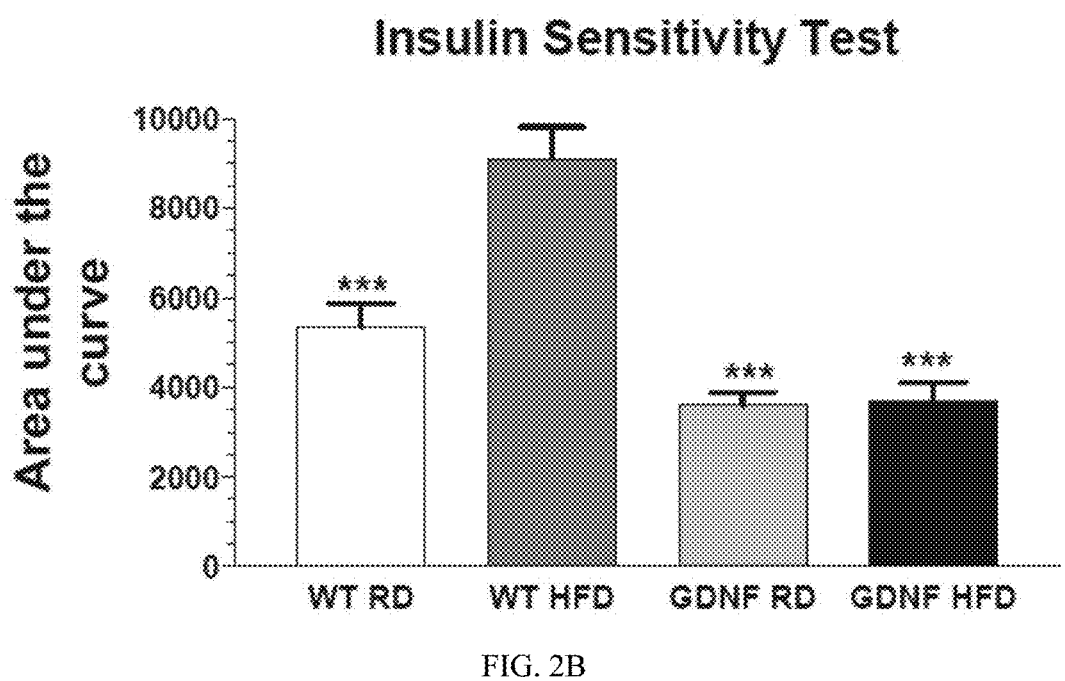

GDNF-Tg Mice Resist High Fat Diet-Induced Glucose Intolerance and Insulin Resistance Diet-induced obesity is frequently associated with glucose intolerance and insulin resistance. Glucose tolerance tests and insulin sensitivity tests were performed in overnight fasted mice 10 weeks after the start of the diets to examine the ability of GDNF to protect against diet-induced insulin resistance. GDNF-tg and WT mice fed the regular diet as well as GDNF-tg mice fed the HFD had low fasting blood glucose, an indication of normal insulin sensitivity, while WT mice fed the HFD had high fasting blood glucose which is a sign of diet-induced insulin resistance (FIG. 2A-2B). After an intraperitoneal injection with 3 mg glucose/kg body weight, blood glucose levels of GDNF-tg mice fed the HFD increased and then came down quickly and did not differ significantly from those of GDNF-tg mice fed the regular diet (FIG. 2A). In contrast, blood glucose levels of WT mice fed the HFD rose higher and remained higher than blood glucose levels of WT and GDNF-tg mice fed the regular diet as well as GDNF-tg mice fed the HFD (FIG. 2A). Comparison of blood glucose curves showed significantly larger (P<0.001) area under the curve for WT mice fed the HFD, but no significant differences between GDNF-tg mice fed the HFD and GDNF-tg mice fed the regular diet (FIG. 2A). As a further indication of protection against diet-induced insulin resistance, blood glucose levels of GDNF-tg mice fed a HFD, like those of GDNF-tg and WT mice fed the regular diet, fell significantly after an intraperitoneal injection with 1IU Humalog insulin/kg body weight while those of WT mice fed the HFD and exhibiting signs of insulin resistance did not change significantly after insulin injection (FIG. 2B). As a result, while blood glucose area under the curves for WT mice fed the HFD were significantly larger (P<0.001) than the curves for WT and GDNF-tg mice fed the regular diet as well as GDNF-tg mice fed the HFD, blood glucose area under for GDNF-tg mice fed the HFD and those fed the regular diet were not significantly different (FIG. 2B).

GDNF-Tg Mice are Protected Against High Fat Diet-Induced Hepatic Steatosis

Figure 3A:
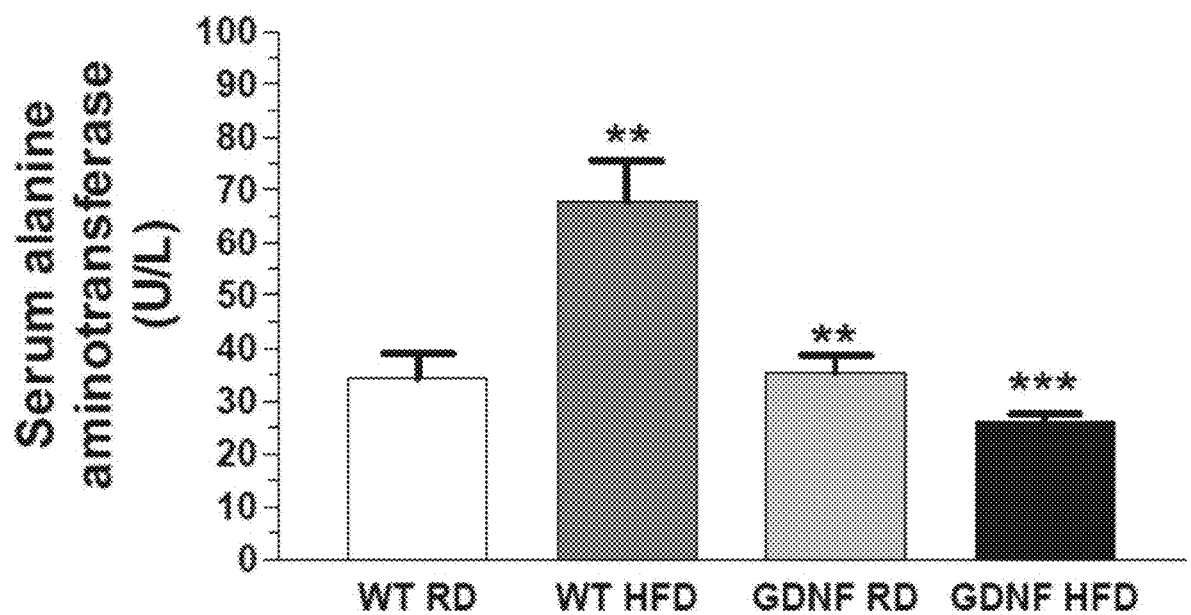
FIG. 3A shows data indicating GDNF-tg mice are protected against high fat diet-induced hepatosteatosis. Serum alanine aminotransferase levels.
Figure 3B:
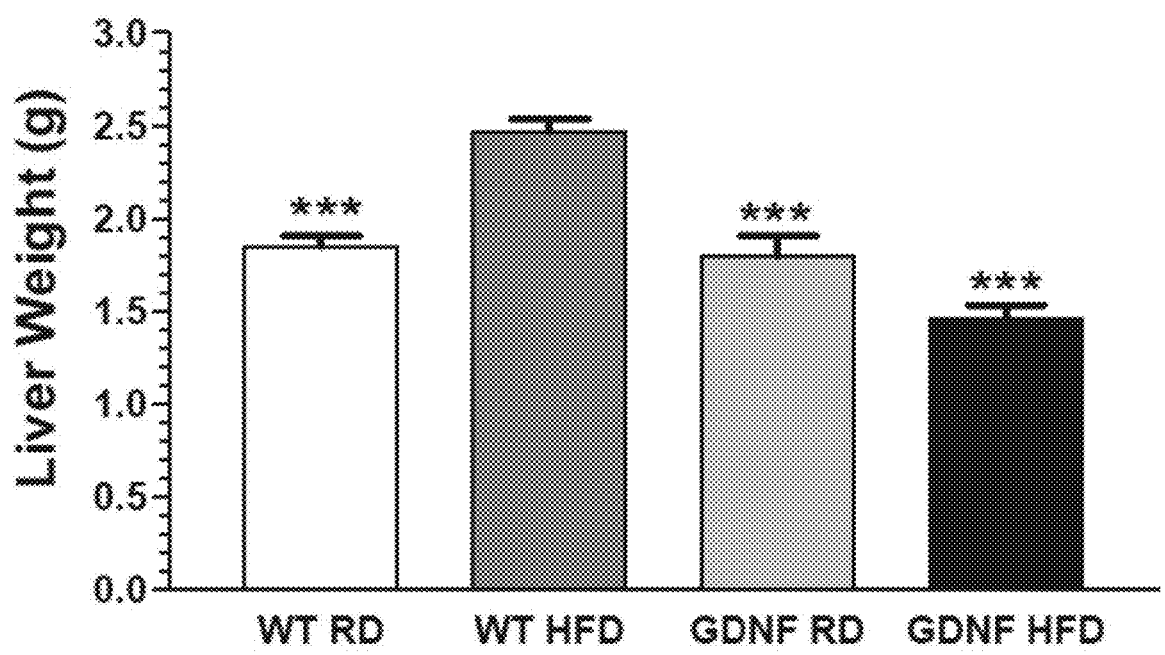
FIG. 3B shows data on liver weights.
Figure 3C:
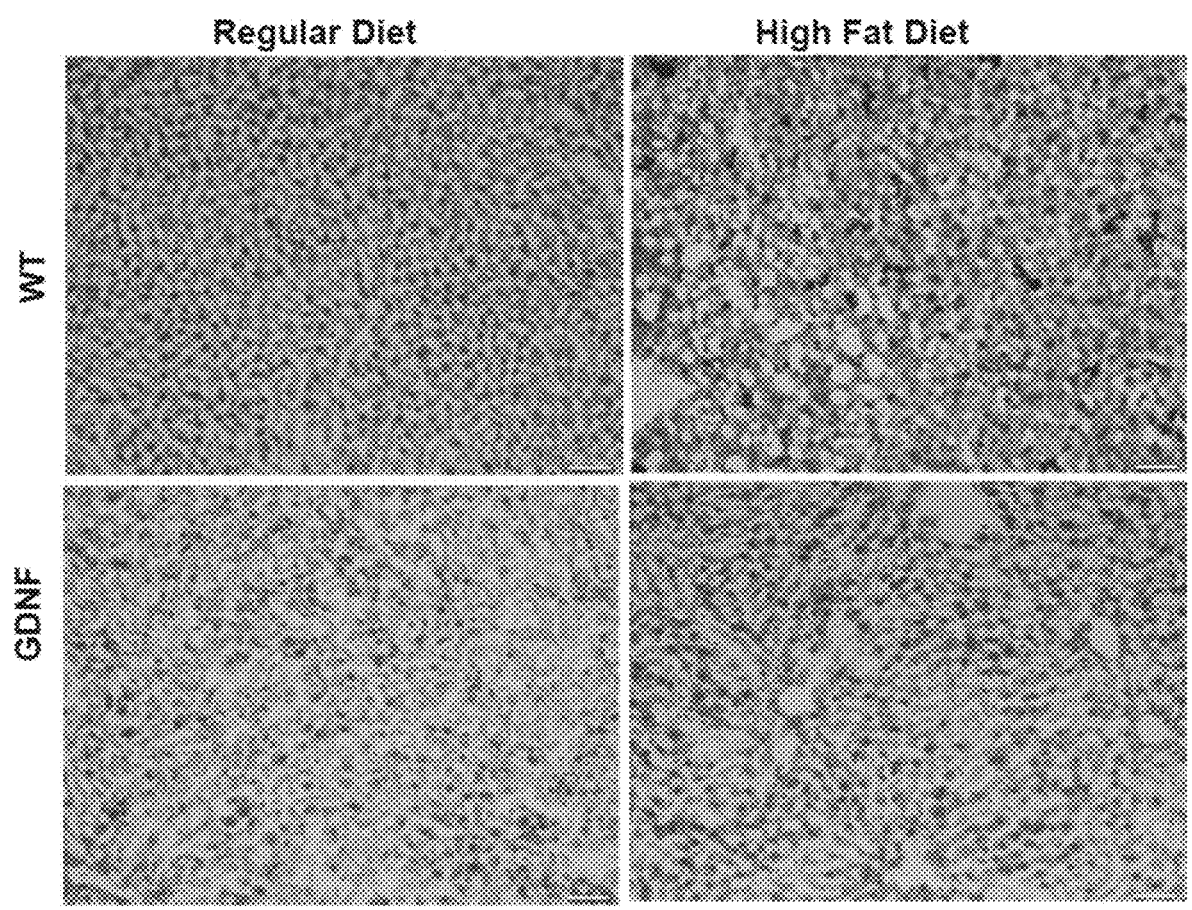
FIG. 3C shows data on liver sections stained with Oil Red-O.
Figure 3D:
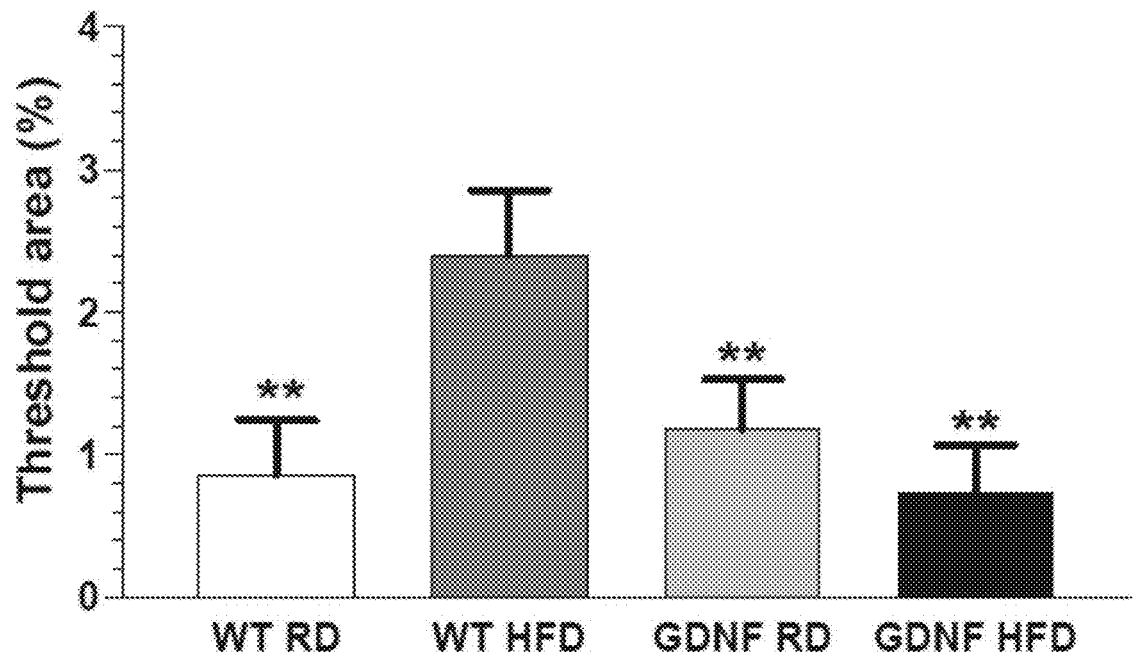
FIG. 3D shows data on comparison of liver Oil Red-O staining intensity.
Figure 3E:
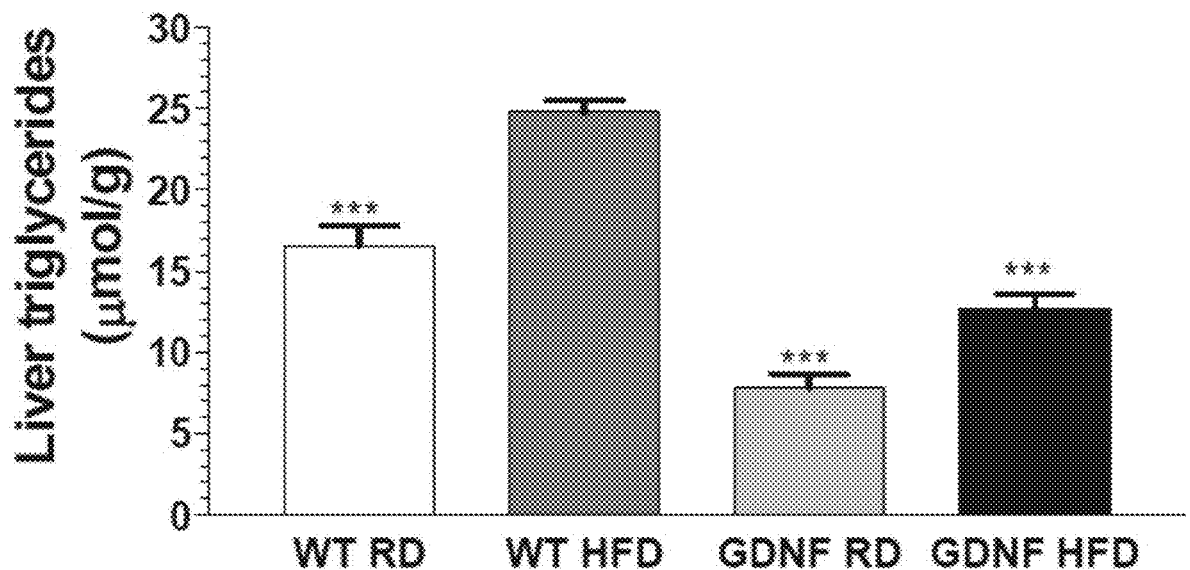
FIG. 3E shows data on liver triglyceride levels in GDNF-tg and WT mice fed a regular diet or HFD for 11 weeks. Data presented are means+SE. *, $P<0.001$; , $P<0.01$, compared to WT HFD mice (n=5-9 mice per group). Scale 50 μm.

Obesity is associated with lipid accumulation (steatosis) in the liver which is a contributing factor for non-alcoholic fatty liver disease (NAFLD), a disease marked by elevated serum levels several liver enzymes including alanine aminotransferase (ALT). To determine if GDNF can protect against HFD-induced hepatic steatosis, ALT levels were assessed in sera from mice fed a regular diet or HFD for 11 weeks. Serum ALT levels of GDNF-tg mice fed the HFD were not significantly different from those of GDNF-tg and WT mice on the regular diet, but were significantly lower (P<0.001) than those of WT mice fed the HFD (FIG. 3A). The effects of the diets were examined on liver weight. Liver weights of GDNF-tg mice fed the HFD and those of GDNF-tg and WT mice fed the regular diet were not significantly different (FIG. 3B). In contrast, liver weights of WT mice fed the HFD were significantly higher than those of WT and GDNF-tg mice fed the regular diet as well as GDNF-tg mice fed the HFD (FIG. 3B). To confirm that the observed differences were due to hepatosteatosis we stained sections of liver from the study mice with Oil Red-O. As is evident from the stained sections (FIG. 3C) there was extensive lipid accumulation in liver from WT mice fed the HFD diet, but very little in liver from GDNF-tg mice fed the HFD as well as GDNF-tg and WT mice fed the regular diet. Densitometric analysis of the staining intensity showed similar low fat accumulation in liver from GDNF-tg mice fed the HFD as well as GDNF-tg and WT mice fed the regular diet, but significantly higher accumulation in liver from WT mice fed the HFD (FIG. 3D). These results were further confirmed by assessing liver triglyceride levels using a colorimetric method (FIG. 3E).

Figure 4A:
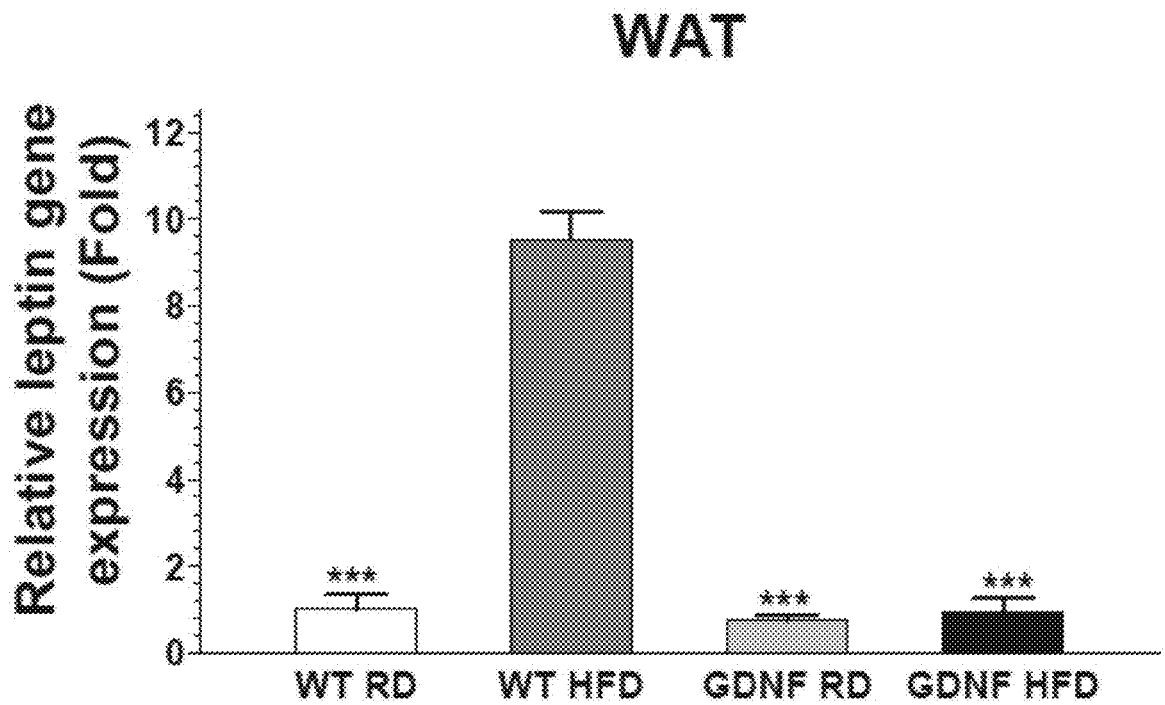
FIG. 4A shows data indicating GDNF-tg mice have lower expression of metabolic genes associated with increased obesity. Analysis of leptin expression in WAT by real-time PCR.
Figure 4B:
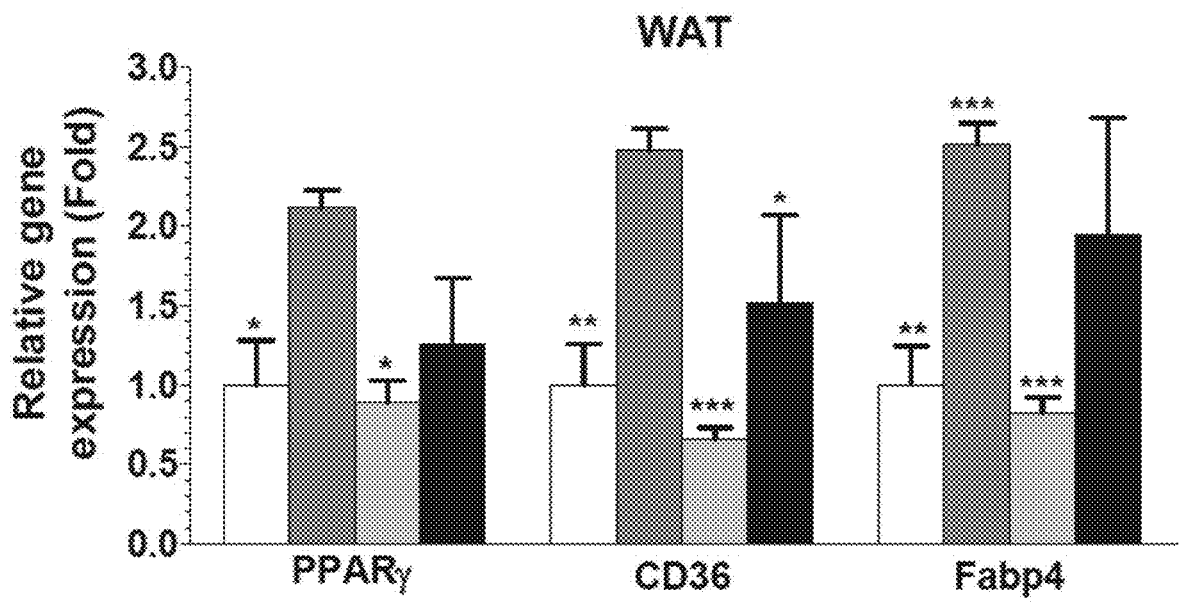
FIG. 4B shows data on analysis by real-time PCR of metabolic gene expression in WAT from GDNF-tg and WT mice fed a regular diet or a HFD for 11 weeks.
Figure 4C:
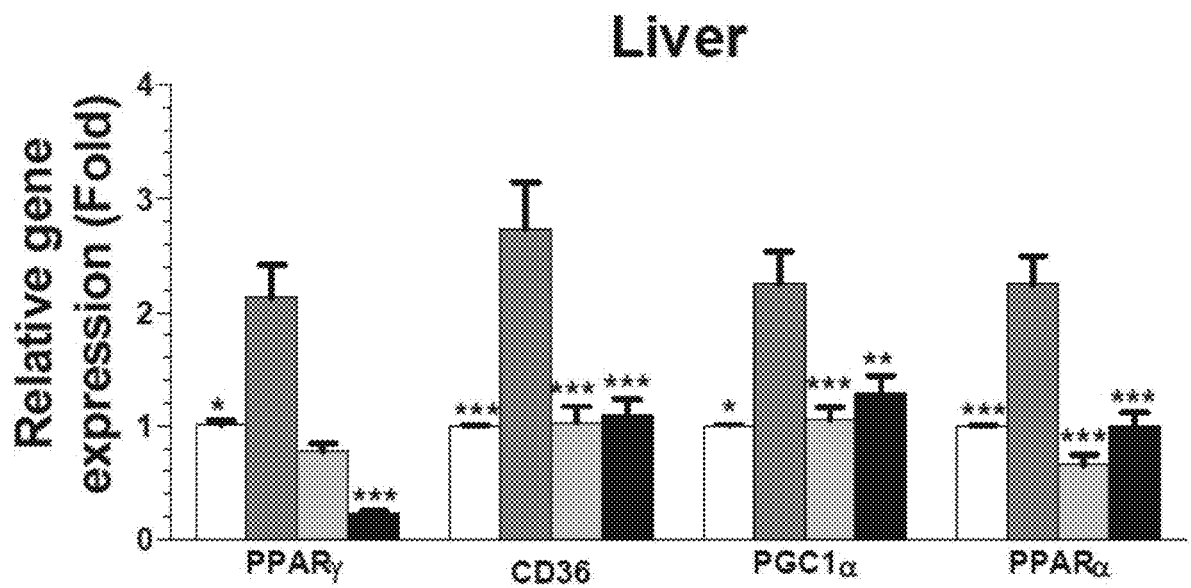
FIG. 4C shows data in liver.
Figure 4D:
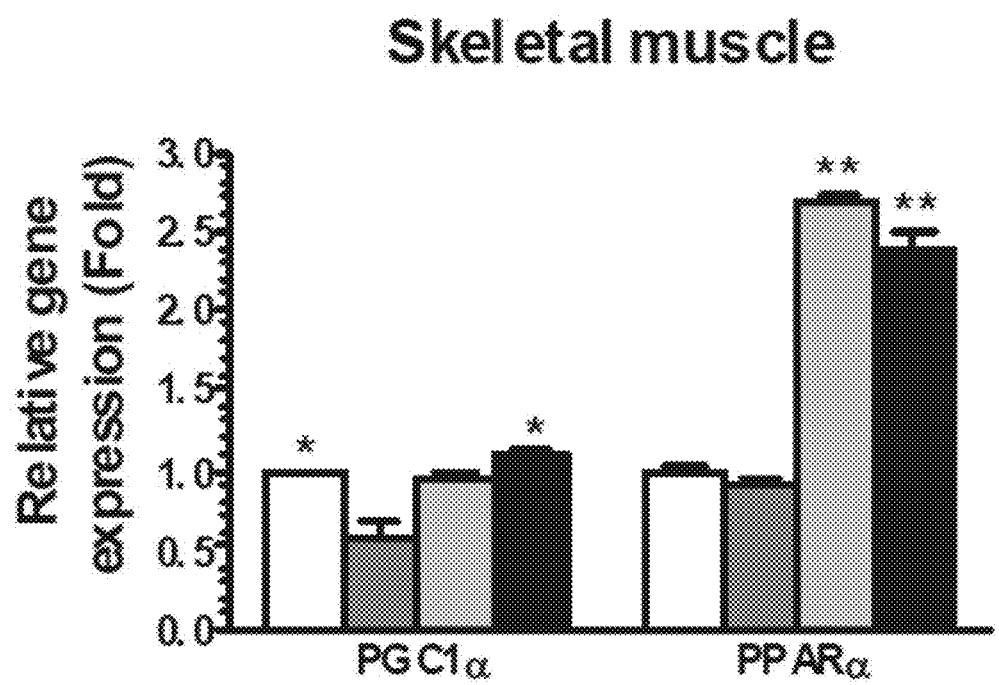
FIG. 4D shows data in skeletal muscles.
Figure 4E:
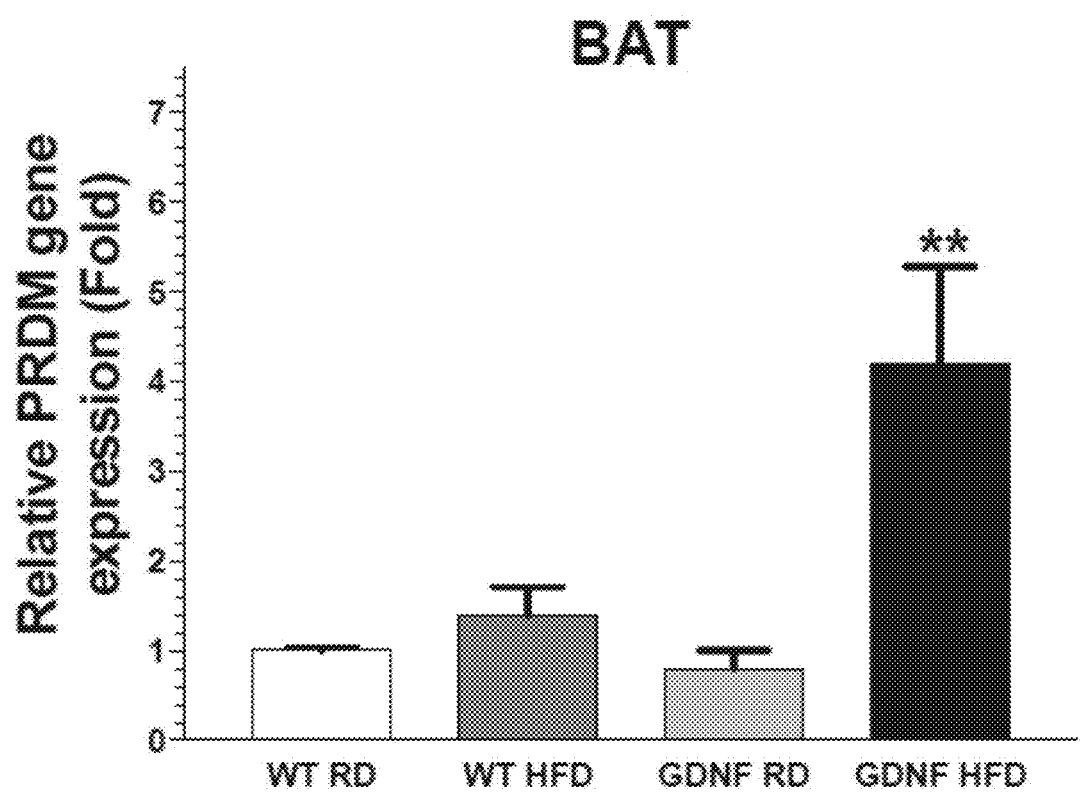
FIG. 4E shows data in BAT.

GDNF-Tg Mice have Lower Expression of Metabolic Genes Associated with Increased Obesity Obesity is associated with altered expression of key metabolic genes in various organs. Several metabolic genes were assessed by real-time PCR the expression levels using RNA isolated from WAT, liver, skeletal muscle and BAT from GDNF-tg and WT mice fed a regular diet or the HFD for 11 weeks. The expression of genes associated with increased adiposity including, leptin, PPARγ, CD36 (fatty acid translocase) and fatty acid binding protein 4 (Fabp4), in WAT in GDNF-tg mice fed the HFD was similar to that in GDNF-tg and WT mice fed the regular diet, but significantly lower than that in WT mice fed the HFD (FIG. 4A-B). In the liver the expression of PPARγ, CD36, PGC1α and PPARγ, whose expression in the liver is increased obesity and insulin resistant states, was not significantly different between GDNF-tg mice fed the HFD diet and GDNF-tg and WT mice fed the regular diet, but was significantly elevated in WT mice fed the HFD (FIG. 4C). PGC1α and PPARα play an important role in oxidative metabolism in skeletal muscles and their expression is associated with improved insulin sensitivity. The expression in skeletal muscles of PGC1α in GDNF-tg mice fed the HFD was similar to that in GDNF-tg and WT mice fed the regular diet, but significantly higher than that in WT mice fed the HFD, while the expression of PPARα in both groups of GDNF-tg mice was significantly higher than that of the WT groups (FIG. 4D). Finally, GDNF-tg mice fed the HFD had significantly higher expression in brown fat of the PR-domain-containing 16 (PRDM16) gene, an early regulator of brown fat fate, that GNDF-tg and WT mice fed a regular diet as well as WT mice fed the HFD (FIG. 4D).

GDNF and its Receptors are Expressed in Human and Murine Adipose Tissue.

Figure 8:
FIG. 8 shows data indicating receptors for GDNF are present in human adipose tissue. Representative photographs of expression of GDNF in WAT glia of WT and GDNF-tg. Human adipocyte expression of GDNF receptors GFR-α and c-Ret is seen. Human tissue was also stained for GDNF and co-localization with glia (stained with glial marker S-100) was determined. Arrows depict glia. Inset shows negative control with minimal background staining.

To study the effects of GDNF in adipose tissue one assesses if its receptors are expressed in human and murine adipose tissue. GDNF signals through the Ret and GFR-1α receptors. Using RT-PCR expression of Ret and GFR-1a was found in (White adipose tissue) WAT of WT and GDNF-tg mice. As seen in FIG. 8, GDNF and its receptors-C-Ret and GFRα1 are expressed on human adipocytes and murine adipose tissue.

GDNF Prevents Adipocyte Differentiation In Vitro.

Figure 5A:
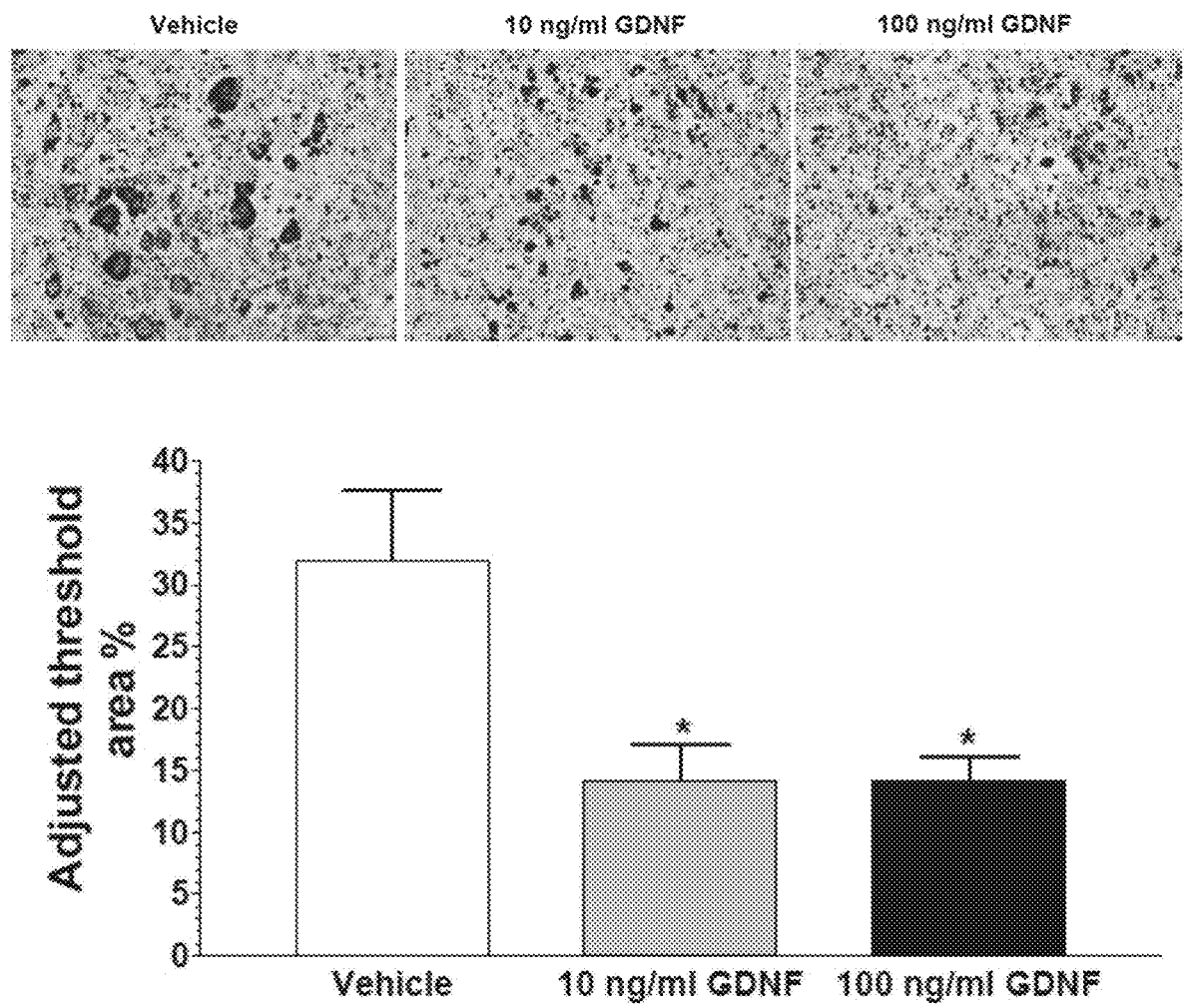
FIG. 5A shows data indicating GDNF suppresses adipogenesis in 3T3-L1 cells. 3T3-L1 cells were exposed to vehicle or GDNF for 7 days in the absence or presence of knock down of Ret (Ret siRNA) and assessed for mature adipocytes using Staining with Oil Red-O. * $P<0.05$,  $P<0.01$, * $P<0.001$ relative to vehicle. GDNF inhibits genes influencing adipocyte differentiation in vitro. 3T3-L1 cells were cultured in the presence or absence of GDNF (10-100 ng/ml) for 3-7 days and assessed for markers of adipocyte differentiation by Real time PCR.** $P<0.01$ ND: Non differentiated.
Figure 5B:
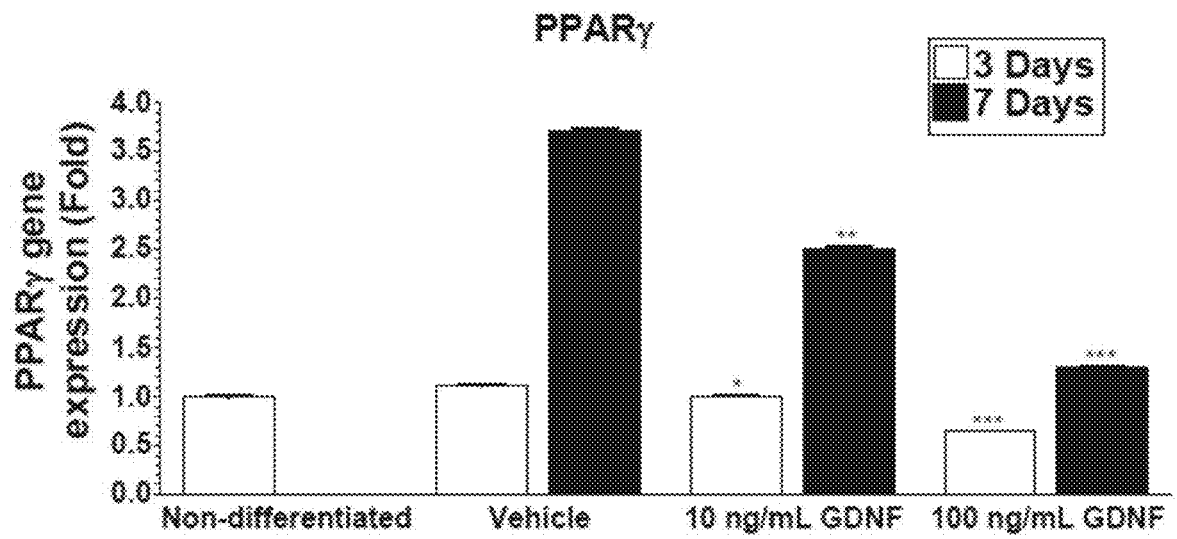
FIG. 5B shows data for the PPARgama gene.
Figure 5C:
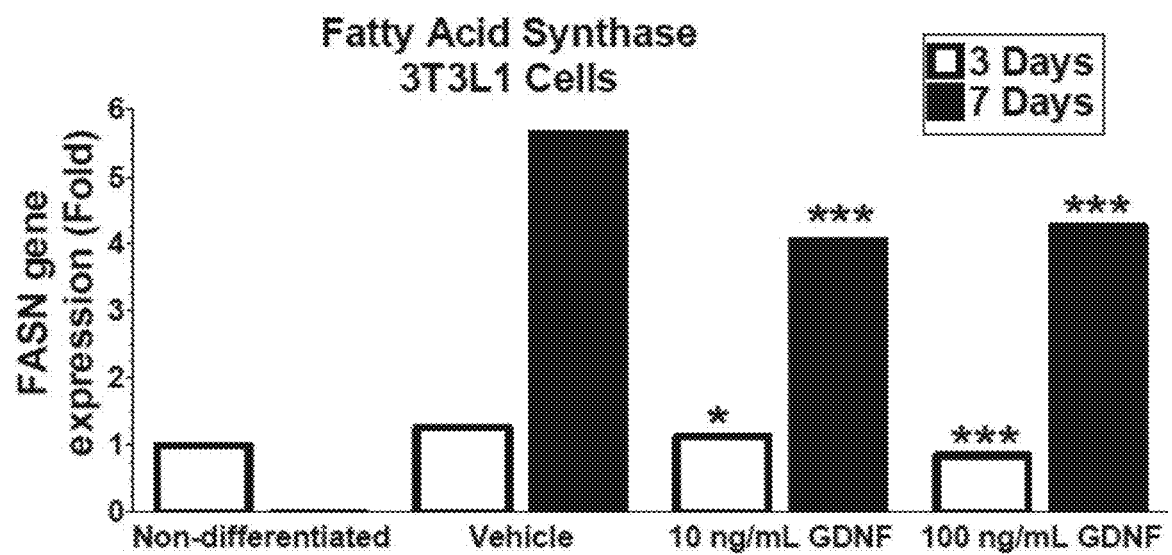
FIG. 5C shows data for the FASN gene.
Figure 5D:
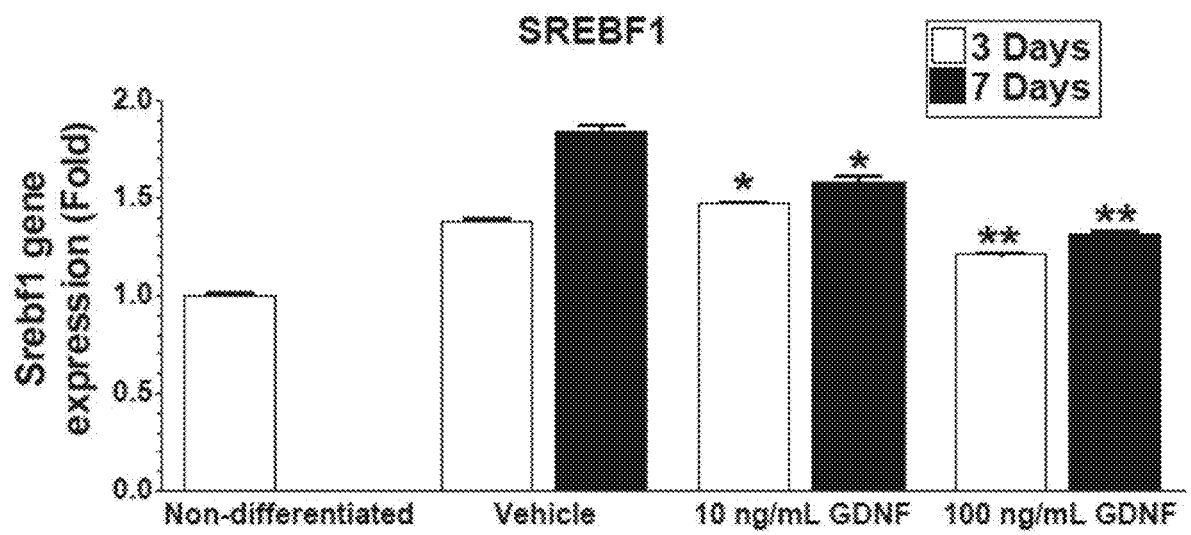
FIG. 5D shows data for the Srebf1 gene.
Figure 5E:
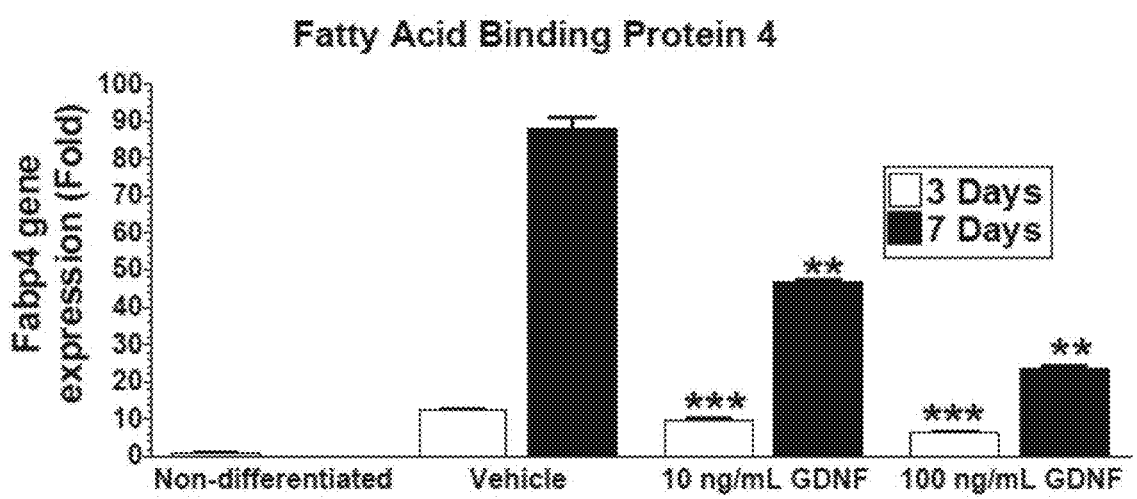
FIG. 5E shows data for the Fabp4 gene.

To study the mechanism of GDNF modulation of adipogenesis, the effects of GDNF were assessed on a in vitro cell culture model of adipocytes-differentiated 3T3-L1 cells. As seen in FIG. 5A, GDNF inhibited adipogenesis as assessed by Oil red-O staining and this was prevented in the presence of knock down of GDNF receptor using Ret siRNA. Further it was found that GDNF inhibited the genes regulating differentiation of 3T3-L1 cells into adipocytes (PPAR-γ, FASN and FABP4, FIG. 5B).

GDNF Enhances MAPK Activation.

Figure 9A:
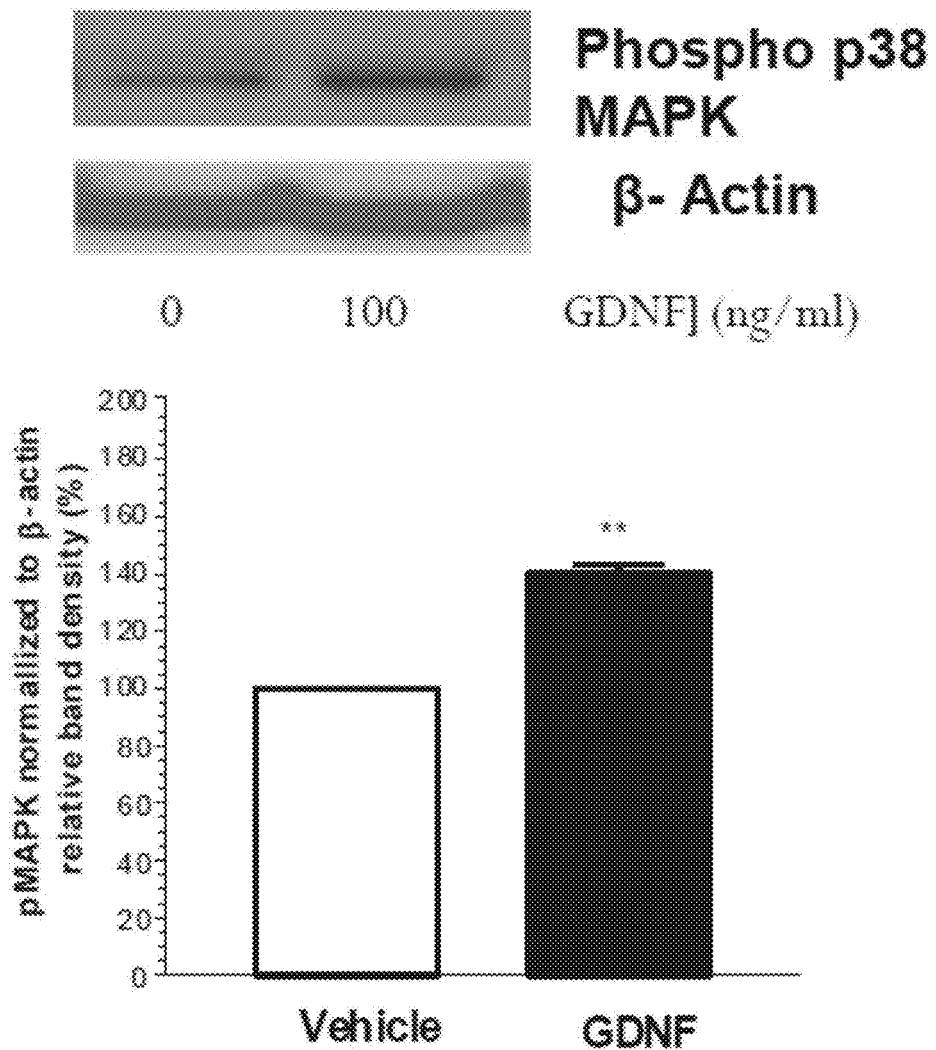
FIG. 9A shows data indicating GDNF activates MAPK: 3T3-L1 cells were serum starved for 12 h followed by treatment with Vehicle or GDNF for 1 h and Western Blot Analysis for pAkt, total Akt, MAPK and β-actin performed.
Figure 9B:
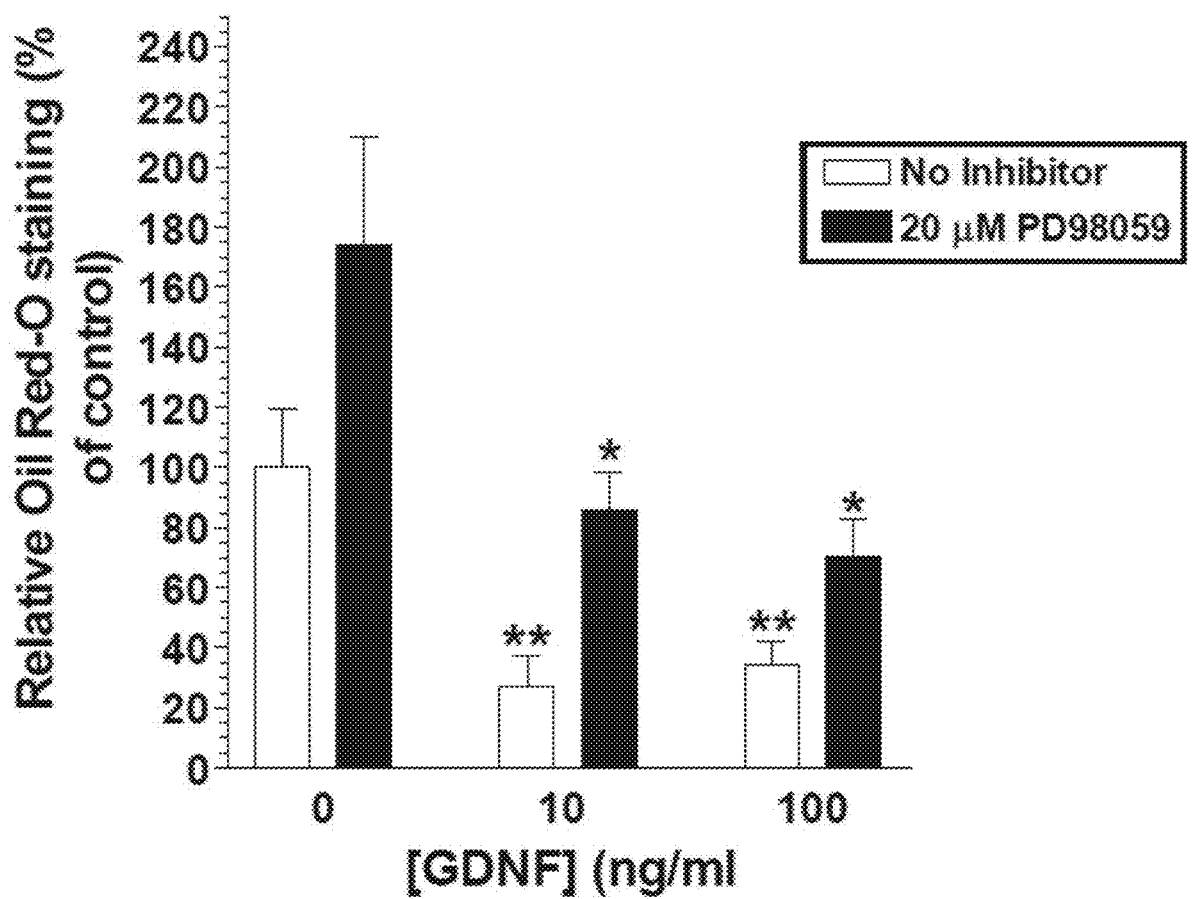
FIG. 9B shows data on GDNF mediated suppression of adipogenesis is prevented by MAPK inhibitor, PD98059. In the presence of MAPK inhibitor there is partial reversal of GDNF mediated inhibition of adipogenesis.

To determine the mechanism of signaling of GDNF induced inhibition of adipocyte differentiation, 3T3-L1 cells were differentiated into adipocytes and assessed for MAPK phosphorylation in the presence or absence of GDNF (10 ng/ml). GDNF induced phosphorylation of MAPK (FIG. 9A). In addition, GDNF mediated inhibition of adipogenesis (Oil Red O staining) was reversed in the presence of the MAPK inhibitor, PD98059 (FIG. 9B).

Intraperitoneal Injection of GDNF Increases Serum GDNF Concentration

Experimental Setup: WT mice were given intraperitoneal injections of either vehicle or recombinant GDNF (2 ug/kg body wt). Serum was obtained 6 h post injection and was assessed for GDNF by enzyme-linked immunosorbant assay (ELISA).

Figure 10:
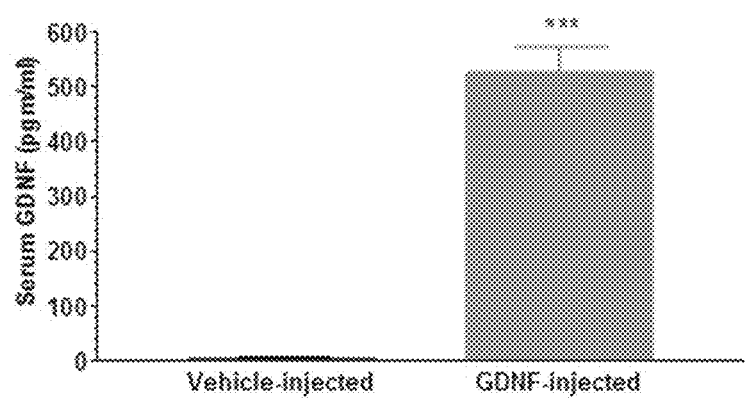
FIG. 10 shows data indicating that intraperitoneal injection of GDNF injection can increase serum GDNF levels.

Results: Mice injected with GDNF exhibited a sustained elevation of serum GDNF for several hours after injection (FIG. 10). In addition this dosage of GDNF resulted in a significant increase in pAKT assessed in WAT of mice injected with GDNF compared to mice injected with vehicle.

GDNF Inhibits Expression of Genes Involved in Adipogenesis and Lipogenesis in 3T3L1 Cells Experimental setup: Adipogenesis was studied in vitro using GDNF applied to 3T3L1 cell cultures. Cells were divided into seven groups. Four were harvested after 3 days, whereas 3 were harvested after 7 days. The 3-day groups consisted of non-differentiated, differentiated control, differentiated+10 ng/mL GDNF, and differentiated+100 ng/mL GDNF. The 7-day groups consisted of differentiated control, differentiated+10 ng/mL GDNF, and differentiated+100 ng/mL GDNF. The relative quantity of gene expression of SREBF1 was then measured in the 3T3L1 cells. All gene expression was analyzed relative to the 3 day undifferentiated group.

Figure 11:
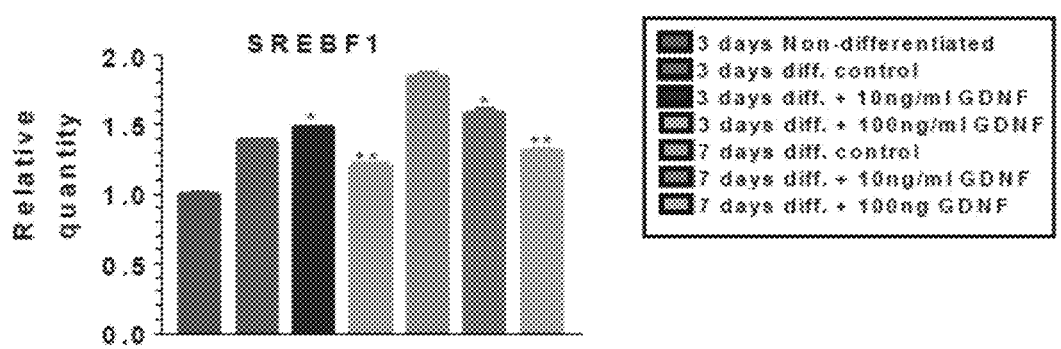
FIG. 11 shows data indicating decrease in SREBF1 relative to control with increasing doses of GDNF.

Results: SREBF1 has been associated with obesity, type 2 diabetes, and dyslipidemia. In FIG. 11, an incremental decrease in SREBF1 relative to control is shown at 7 days with increasing doses of GDNF (long/mL and 100 ng/mL). At 3 days, however, 10 ng/mL GDNF increase SREBF1 relative to control.

The invention claimed is:

1. A method of treating steatohepatitis comprising administering an effective amount of a polypeptide comprising SEQ ID NO: 7 to a human subject in need thereof.

2. The method of claim 1, wherein the subject is diagnosed with a fatty liver and has body fat in excess of 20% of total body weight.

3. A method of treating steatohepatitis comprising administering an effective amount of a polypeptide comprising SEQ ID NO: 8 to a human subject in need thereof.

4. The method of claim 3, wherein the subject is diagnosed with a fatty liver and has body fat in excess of 20% of total body weight.

5. A method of treating steatohepatitis comprising administering an effective amount of a polypeptide comprising SEQ ID NO: 9 to a human subject in need thereof.

6. The method of claim 5, wherein the subject is diagnosed with a fatty liver and has body fat in excess of 20% of total body weight.

7. A method of treating steatohepatitis comprising administering an effective amount of a polypeptide comprising SEQ ID NO: 10 to a human subject in need thereof.

8. The method of claim 7, wherein the subject is diagnosed with a fatty liver and has body fat in excess of 20% of total body weight.

* * * * *

SEQUENCE LISTING

```
<160> NUMBER OF SEQ ID NOS: 10

<210> SEQ ID NO 1
<211> LENGTH: 211
<212> TYPE: PRT
<213> ORGANISM: Homo sapiens
<220> FEATURE:
<221> NAME/KEY: VARIANT
<222> LOCATION: (1)..(211)
<223> OTHER INFORMATION: Human GDNF

<400> SEQUENCE: 1

Met Lys Leu Trp Asp Val Val Ala Val Cys Leu Val Leu Leu His Thr
1               5                   10                  15

Ala Ser Ala Phe Pro Leu Pro Ala Gly Lys Arg Pro Pro Glu Ala Pro
            20                  25                  30

Ala Glu Asp Arg Ser Leu Gly Arg Arg Arg Ala Pro Phe Ala Leu Ser
        35                  40                  45

Ser Asp Ser Asn Met Pro Glu Asp Tyr Pro Asp Gln Phe Asp Asp Val
    50                  55                  60

Met Asp Phe Ile Gln Ala Thr Ile Lys Arg Leu Lys Arg Ser Pro Asp
65                  70                  75                  80

Lys Gln Met Ala Val Leu Pro Arg Arg Glu Arg Asn Arg Gln Ala Ala
                85                  90                  95

Ala Ala Asn Pro Glu Asn Ser Arg Gly Lys Gly Arg Arg Gly Gln Arg
            100                 105                 110

Gly Lys Asn Arg Gly Cys Val Leu Thr Ala Ile His Leu Asn Val Thr
        115                 120                 125

Asp Leu Gly Leu Gly Tyr Glu Thr Lys Glu Glu Leu Ile Phe Arg Tyr
    130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Asp Lys Val Gly Gln
                165                 170                 175

Ala Cys Cys Arg Pro Ile Ala Phe Asp Asp Leu Ser Phe Leu Asp
            180                 185                 190
```

-continued

```
Asp Asn Leu Val Tyr His Ile Leu Arg Lys His Ser Ala Lys Arg Cys
            195                 200                 205

Gly Cys Ile
        210

<210> SEQ ID NO 2
<211> LENGTH: 185
<212> TYPE: PRT
<213> ORGANISM: Homo sapiens
<220> FEATURE:
<221> NAME/KEY: VARIANT
<222> LOCATION: (1)..(185)
<223> OTHER INFORMATION: Human GDNF

<400> SEQUENCE: 2

Met Lys Leu Trp Asp Val Val Ala Val Cys Leu Val Leu Leu His Thr
1               5                   10                  15

Ala Ser Ala Phe Pro Leu Pro Ala Ala Asn Met Pro Glu Asp Tyr Pro
            20                  25                  30

Asp Gln Phe Asp Asp Val Met Asp Phe Ile Gln Ala Thr Ile Lys Arg
        35                  40                  45

Leu Lys Arg Ser Pro Asp Lys Gln Met Ala Val Leu Pro Arg Arg Glu
50                  55                  60

Arg Asn Arg Gln Ala Ala Ala Ala Asn Pro Glu Asn Ser Arg Gly Lys
65                  70                  75                  80

Gly Arg Arg Gly Gln Arg Gly Lys Asn Arg Gly Cys Val Leu Thr Ala
                85                  90                  95

Ile His Leu Asn Val Thr Asp Leu Gly Leu Gly Tyr Glu Thr Lys Glu
            100                 105                 110

Glu Leu Ile Phe Arg Tyr Cys Ser Gly Ser Cys Asp Ala Ala Glu Thr
        115                 120                 125

Thr Tyr Asp Lys Ile Leu Lys Asn Leu Ser Arg Asn Arg Arg Leu Val
130                 135                 140

Ser Asp Lys Val Gly Gln Ala Cys Cys Arg Pro Ile Ala Phe Asp Asp
145                 150                 155                 160

Asp Leu Ser Phe Leu Asp Asp Asn Leu Val Tyr His Ile Leu Arg Lys
                165                 170                 175

His Ser Ala Lys Arg Cys Gly Cys Ile
            180                 185

<210> SEQ ID NO 3
<211> LENGTH: 228
<212> TYPE: PRT
<213> ORGANISM: Homo sapiens
<220> FEATURE:
<221> NAME/KEY: VARIANT
<222> LOCATION: (1)..(228)
<223> OTHER INFORMATION: Human GDNF

<400> SEQUENCE: 3

Met Gln Ser Leu Pro Asn Ser Asn Gly Ala Ala Gly Arg Asp Phe
1               5                   10                  15

Lys Met Lys Leu Trp Asp Val Val Ala Val Cys Leu Val Leu Leu His
            20                  25                  30

Thr Ala Ser Ala Phe Pro Leu Pro Ala Gly Lys Arg Pro Pro Glu Ala
        35                  40                  45

Pro Ala Glu Asp Arg Ser Leu Gly Arg Arg Arg Ala Pro Phe Ala Leu
50                  55                  60

Ser Ser Asp Ser Asn Met Pro Glu Asp Tyr Pro Asp Gln Phe Asp Asp
```

```
                65                  70                  75                  80
Val Met Asp Phe Ile Gln Ala Thr Ile Lys Arg Leu Lys Arg Ser Pro
                    85                  90                  95

Asp Lys Gln Met Ala Val Leu Pro Arg Arg Glu Arg Asn Arg Gln Ala
                100                 105                 110

Ala Ala Ala Asn Pro Glu Asn Ser Arg Gly Lys Gly Arg Arg Gly Gln
            115                 120                 125

Arg Gly Lys Asn Arg Gly Cys Val Leu Thr Ala Ile His Leu Asn Val
        130                 135                 140

Thr Asp Leu Gly Leu Gly Tyr Glu Thr Lys Glu Glu Leu Ile Phe Arg
145                 150                 155                 160

Tyr Cys Ser Gly Ser Cys Asp Ala Ala Glu Thr Thr Tyr Asp Lys Ile
                165                 170                 175

Leu Lys Asn Leu Ser Arg Asn Arg Arg Leu Val Ser Asp Lys Val Gly
                180                 185                 190

Gln Ala Cys Cys Arg Pro Ile Ala Phe Asp Asp Asp Leu Ser Phe Leu
            195                 200                 205

Asp Asp Asn Leu Val Tyr His Ile Leu Arg Lys His Ser Ala Lys Arg
        210                 215                 220

Cys Gly Cys Ile
225

<210> SEQ ID NO 4
<211> LENGTH: 202
<212> TYPE: PRT
<213> ORGANISM: Homo sapiens
<220> FEATURE:
<221> NAME/KEY: VARIANT
<222> LOCATION: (1)..(202)
<223> OTHER INFORMATION: Human GDNF

<400> SEQUENCE: 4

Met Gln Ser Leu Pro Asn Ser Asn Gly Ala Ala Gly Arg Asp Phe
1               5                   10                  15

Lys Met Lys Leu Trp Asp Val Val Ala Val Cys Leu Val Leu Leu His
                20                  25                  30

Thr Ala Ser Ala Phe Pro Leu Pro Ala Ala Asn Met Pro Glu Asp Tyr
            35                  40                  45

Pro Asp Gln Phe Asp Asp Val Met Asp Phe Ile Gln Ala Thr Ile Lys
        50                  55                  60

Arg Leu Lys Arg Ser Pro Asp Lys Gln Met Ala Val Leu Pro Arg Arg
65                  70                  75                  80

Glu Arg Asn Arg Gln Ala Ala Ala Ala Asn Pro Glu Asn Ser Arg Gly
                85                  90                  95

Lys Gly Arg Arg Gly Gln Arg Gly Lys Asn Arg Gly Cys Val Leu Thr
                100                 105                 110

Ala Ile His Leu Asn Val Thr Asp Leu Gly Leu Gly Tyr Glu Thr Lys
            115                 120                 125

Glu Glu Leu Ile Phe Arg Tyr Cys Ser Gly Ser Cys Asp Ala Ala Glu
        130                 135                 140

Thr Thr Tyr Asp Lys Ile Leu Lys Asn Leu Ser Arg Asn Arg Arg Leu
145                 150                 155                 160

Val Ser Asp Lys Val Gly Gln Ala Cys Cys Arg Pro Ile Ala Phe Asp
                165                 170                 175

Asp Asp Leu Ser Phe Leu Asp Asp Asn Leu Val Tyr His Ile Leu Arg
            180                 185                 190
```

Lys His Ser Ala Lys Arg Cys Gly Cys Ile
        195                 200

<210> SEQ ID NO 5
<211> LENGTH: 211
<212> TYPE: PRT
<213> ORGANISM: Homo sapiens
<220> FEATURE:
<221> NAME/KEY: MISC_FEATURE
<223> OTHER INFORMATION: Where CTT = LEU
<220> FEATURE:
<221> NAME/KEY: MISC_FEATURE
<223> OTHER INFORMATION: Where CCG = PRO
<220> FEATURE:
<221> NAME/KEY: MISC_FEATURE
<223> OTHER INFORMATION: Where GAG = GLU

<400> SEQUENCE: 5

Met Lys Leu Trp Asp Val Val Ala Val Cys Leu Val Leu Leu His Thr
1               5                   10                  15

Ala Ser Ala Phe Pro Leu Pro Ala Gly Lys Arg Pro Pro Glu Ala Pro
            20                  25                  30

Ala Glu Asp Arg Ser Leu Gly Arg Arg Arg Ala Pro Phe Ala Leu Ser
        35                  40                  45

Ser Asp Ser Asn Met Pro Glu Asp Tyr Pro Asp Gln Phe Asp Asp Val
    50                  55                  60

Met Asp Phe Ile Gln Ala Thr Ile Lys Arg Leu Lys Arg Ser Pro Asp
65                  70                  75                  80

Lys Gln Met Ala Val Leu Pro Arg Arg Glu Arg Asn Arg Gln Ala Ala
                85                  90                  95

Ala Ala Asn Pro Glu Asn Ser Arg Gly Lys Gly Arg Arg Gly Gln Arg
            100                 105                 110

Gly Lys Asn Arg Gly Cys Val Leu Thr Ala Ile His Leu Asn Val Thr
        115                 120                 125

Asp Leu Gly Leu Gly Tyr Glu Thr Lys Glu Glu Leu Ile Phe Arg Tyr
    130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Thr Asp Lys Val Gly Gln
                165                 170                 175

Ala Cys Cys Arg Pro Ile Ala Phe Asp Asp Asp Leu Ser Phe Leu Asp
            180                 185                 190

Asp Asn Leu Val Tyr His Ile Leu Arg Lys His Ser Ala Lys Arg Cys
        195                 200                 205

Gly Cys Ile
    210

<210> SEQ ID NO 6
<211> LENGTH: 211
<212> TYPE: PRT
<213> ORGANISM: Rattus norvegicus
<220> FEATURE:
<221> NAME/KEY: MISC_FEATURE
<223> OTHER INFORMATION: Where CTT = LEU
<220> FEATURE:
<221> NAME/KEY: MISC_FEATURE
<223> OTHER INFORMATION: Where CCG = PRO
<220> FEATURE:
<221> NAME/KEY: MISC_FEATURE
<223> OTHER INFORMATION: Where GAG = GLU

<400> SEQUENCE: 6

```
Met Lys Leu Trp Asp Val Val Ala Val Cys Leu Val Leu Leu His Thr
1               5                   10                  15

Ala Ser Ala Phe Pro Leu Pro Ala Gly Lys Arg Leu Leu Glu Ala Pro
            20                  25                  30

Ala Glu Asp His Ser Leu Gly His Arg Arg Val Pro Phe Ala Leu Thr
        35                  40                  45

Ser Asp Ser Asn Met Pro Glu Asp Tyr Pro Asp Gln Phe Asp Asp Val
50                  55                  60

Met Asp Phe Ile Gln Ala Thr Ile Lys Arg Leu Lys Arg Ser Pro Asp
65                  70                  75                  80

Lys Gln Ala Ala Ala Leu Pro Arg Arg Glu Arg Asn Arg Gln Ala Ala
                85                  90                  95

Ala Ala Ser Pro Glu Asn Ser Arg Gly Lys Gly Arg Gly Gln Arg
                100                 105                 110

Gly Lys Asn Arg Gly Cys Val Leu Thr Ala Ile His Leu Asn Val Thr
        115                 120                 125

Asp Leu Gly Leu Gly Tyr Glu Thr Lys Glu Glu Leu Ile Phe Arg Tyr
    130                 135                 140

Cys Ser Gly Ser Cys Glu Ala Ala Glu Thr Met Tyr Asp Lys Ile Leu
145                 150                 155                 160

Lys Asn Leu Ser Arg Ser Arg Arg Leu Thr Ser Asp Lys Val Gly Gln
                165                 170                 175

Ala Cys Cys Arg Pro Val Ala Phe Asp Asp Leu Ser Phe Leu Asp
                180                 185                 190

Asp Ser Leu Val Tyr His Ile Leu Arg Lys His Ser Ala Lys Arg Cys
            195                 200                 205

Gly Cys Ile
        210

<210> SEQ ID NO 7
<211> LENGTH: 134
<212> TYPE: PRT
<213> ORGANISM: Homo sapiens
<220> FEATURE:
<221> NAME/KEY: MISC_FEATURE
<223> OTHER INFORMATION: Where CTT = LEU
<220> FEATURE:
<221> NAME/KEY: MISC_FEATURE
<223> OTHER INFORMATION: Where CCG = PRO
<220> FEATURE:
<221> NAME/KEY: MISC_FEATURE
<223> OTHER INFORMATION: Where GAG = GLU

<400> SEQUENCE: 7

Ser Pro Asp Lys Gln Met Ala Val Leu Pro Arg Arg Glu Arg Asn Arg
1               5                   10                  15

Gln Ala Ala Ala Ala Asn Pro Glu Asn Ser Arg Gly Lys Gly Arg Arg
            20                  25                  30

Gly Gln Arg Gly Lys Asn Arg Gly Cys Val Leu Thr Ala Ile His Leu
        35                  40                  45

Asn Val Thr Asp Leu Gly Leu Gly Tyr Glu Thr Lys Glu Glu Leu Ile
    50                  55                  60

Phe Arg Tyr Cys Ser Gly Ser Cys Asp Ala Ala Glu Thr Thr Tyr Asp
65                  70                  75                  80

Lys Ile Leu Lys Asn Leu Ser Arg Asn Arg Arg Leu Val Thr Asp Lys
                85                  90                  95

Val Gly Gln Ala Cys Cys Arg Pro Ile Ala Phe Asp Asp Asp Leu Ser
```

```
                    100                 105                 110
Phe Leu Asp Asp Asn Leu Val Tyr His Ile Leu Arg Lys His Ser Ala
            115                 120                 125

Lys Arg Cys Gly Cys Ile
        130

<210> SEQ ID NO 8
<211> LENGTH: 114
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Where CTT = LEU
<220> FEATURE:
<221> NAME/KEY: MISC_FEATURE
<223> OTHER INFORMATION: Where CCG = PRO
<220> FEATURE:
<221> NAME/KEY: MISC_FEATURE
<223> OTHER INFORMATION: Where GAG = GLU

<400> SEQUENCE: 8

Met Ser Pro Glu Asn Ser Arg Gly Lys Gly Arg Gly Gln Arg Gly
1               5                   10                  15

Lys Asn Arg Gly Cys Val Leu Thr Ala Ile His Leu Asn Val Thr Asp
                20                  25                  30

Leu Gly Leu Gly Tyr Glu Thr Asn Glu Glu Leu Ile Phe Arg Tyr Cys
            35                  40                  45

Ser Gly Ser Cys Asp Ala Ala Glu Thr Thr Tyr Asp Lys Ile Leu Lys
50                  55                  60

Asn Leu Ser Arg Asn Arg Arg Leu Val Thr Asp Lys Val Gly Gln Ala
65                  70                  75                  80

Cys Cys Arg Pro Ile Ala Phe Asp Asp Asp Leu Ser Phe Leu Asp Asp
                85                  90                  95

Asn Leu Val Tyr His Ile Leu Arg Lys His Ser Ala Lys Arg Cys Gly
            100                 105                 110

Cys Ile

<210> SEQ ID NO 9
<211> LENGTH: 103
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Where CTT = LEU
<220> FEATURE:
<221> NAME/KEY: MISC_FEATURE
<223> OTHER INFORMATION: Where CCG = PRO
<220> FEATURE:
<221> NAME/KEY: MISC_FEATURE
<223> OTHER INFORMATION: Where GAg = GLU

<400> SEQUENCE: 9

Arg Gly Gln Arg Gly Lys Asn Arg Gly Cys Val Leu Thr Ala Ile His
1               5                   10                  15

Leu Asn Val Thr Asp Leu Gly Leu Gly Tyr Glu Thr Lys Glu Glu Leu
                20                  25                  30

Ile Phe Arg Tyr Cys Ser Gly Ser Cys Asp Ala Ala Glu Thr Thr Tyr
            35                  40                  45

Asp Lys Ile Leu Lys Asn Leu Ser Arg Asn Arg Arg Leu Val Thr Asp
```

```
                50                  55                  60
Lys Val Gly Gln Ala Cys Cys Arg Pro Ile Ala Phe Asp Asp Leu
 65                  70                  75                  80

Ser Phe Leu Asp Asp Asn Leu Val Tyr His Ile Leu Arg Lys His Ser
                 85                  90                  95

Ala Lys Arg Cys Gly Cys Ile
            100

<210> SEQ ID NO 10
<211> LENGTH: 93
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: Where CTT = LEU
<220> FEATURE:
<221> NAME/KEY: MISC_FEATURE
<223> OTHER INFORMATION: Where CCG = PRO
<220> FEATURE:
<221> NAME/KEY: MISC_FEATURE
<223> OTHER INFORMATION: Where GAg = GLU

<400> SEQUENCE: 10

Cys Val Leu Thr Ala Ile His Leu Asn Val Thr Asp Leu Gly Leu Gly
  1               5                  10                  15

Tyr Glu Thr Lys Glu Glu Leu Ile Phe Arg Tyr Cys Ser Gly Ser Cys
                 20                  25                  30

Asp Ala Ala Glu Thr Thr Tyr Asp Lys Ile Leu Lys Asn Leu Ser Arg
             35                  40                  45

Asn Arg Arg Leu Val Thr Asp Lys Val Gly Gln Ala Cys Cys Arg Pro
 50                  55                  60

Ile Ala Phe Asp Asp Leu Ser Phe Leu Asp Asp Asn Leu Val Tyr
 65                  70                  75                  80

His Ile Leu Arg Lys His Ser Ala Lys Arg Cys Gly Cys
                 85                  90
```